US008034997B2

(12) United States Patent
Bogdanova et al.

(10) Patent No.: US 8,034,997 B2
(45) Date of Patent: Oct. 11, 2011

(54) NUCLEOTIDE SEQUENCES ENCODING INSECTICIDAL PROTEINS

(75) Inventors: Natalia N. Bogdanova, Frontenac, MO (US); David R. Corbin, Chesterfield, MO (US); Thomas M. Malvar, North Stonington, CT (US); Frederick J. Perlak, St. Louis, MO (US); James K. Roberts, St. Louis, MO (US); Charles P. Romano, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 236 days.

(21) Appl. No.: 12/064,875

(22) PCT Filed: Aug. 30, 2006

(86) PCT No.: PCT/US2006/033868

§ 371 (c)(1), (2), (4) Date: Feb. 26, 2008

(87) PCT Pub. No.: WO2007/027777
PCT Pub. Date: Mar. 8, 2007

(65) Prior Publication Data

US 2009/0238798 A1 Sep. 24, 2009

Related U.S. Application Data

(60) Provisional application No. 60/713,144, filed on Aug. 31, 2005.

(51) Int. Cl.

| | |
|---|---|
| *C12N 15/82* | (2006.01) |
| *C12N 15/32* | (2006.01) |
| *A01N 37/18* | (2006.01) |
| *A01H 5/00* | (2006.01) |
| *A01H 5/10* | (2006.01) |
| *C07K 14/325* | (2006.01) |

(52) U.S. Cl. ..................... 800/302; 536/23.71; 530/350; 435/320.1; 514/4.5

(58) Field of Classification Search ........................ None
See application file for complete search history.

(56) References Cited

U.S. PATENT DOCUMENTS

| | | | |
|---|---|---|---|
| 5,055,294 | A | 10/1991 | Gilroy |
| 5,128,130 | A | 7/1992 | Gilroy et al. |
| 5,689,052 | A | 11/1997 | Brown et al. |
| 6,180,774 | B1 | 1/2001 | Brown et al. |
| 6,962,705 | B2 | 11/2005 | Malvar et al. |
| 2004/0093637 | A1 | 5/2004 | Malvar et al. |

FOREIGN PATENT DOCUMENTS

| | | | |
|---|---|---|---|
| CN | 1393561 | | 1/2003 |
| EP | 0 385 962 | A1 | 9/1990 |
| EP | 1 103 616 | A2 | 5/2001 |
| WO | WO 95/06730 | A1 | 3/1995 |
| WO | WO 95/24492 | A1 | 9/1995 |
| WO | WO 95/30752 | A1 | 11/1995 |
| WO | WO 95/30753 | A1 | 11/1995 |
| WO | WO 98/22595 | A1 | 5/1998 |
| WO | WO 00/26391 | A1 | 5/2000 |
| WO | WO 02/14517 | * | 2/2002 |
| WO | WO 02/14517 | A1 | 2/2002 |
| WO | WO 02/15701 | | 2/2002 |
| WO | WO 03/093484 | A1 | 11/2003 |

OTHER PUBLICATIONS

Chambers et al., "Isolation and characterization of a novel insecticidal crystal protein gene from *Bacillus thuringiensis* subsp. Aizawai", *J. Bacteriol*., 173:3966-3976, Jul. 1991.

Crickmore et al., "Revision of the nomenclature for the *Bacillus thuringiensis* pesticidal crystal proteins", *Microbiology and Molecular Biology Reviews*, 62(3):807-813, Sep. 1998.

Honee et al., "The C-terminal domain of the toxic fragment of a *Bacillus thuringiensis* crystal protein determines receptor binding", *Mol. Microbiol*., 5(11):2799-2806, Nov. 1991.

Kota et al., "Overexpression of the *Bacillus thuringiensis* (Bt) Cry2Aa2 protein in chloroplasts confers resistance to plants against susceptible and Bt-resistant insects", *Proc. Natl. Acad. Sci*., 96(5):1840-1845, Mar. 2, 1999.

Lee et al., "Location of a *Bombyx mori* receptor binding region on *Bacillus thuringiensis* delta-endotoxin," *J. Biol. Chem*., 15(5):3115-3121, Feb. 1992.

Perlak et al., "Genetically improved potatoes: protection from damage by Colorado potato beetles", *Plant. Mol. Biol*., 22(2):313-321, May 1993.

Perlak et al., "Insect resistant cotton plants", *Biotechnology*, 8(10):939-943, Oct. 1990.

Schnepf et al., "Specificity-determining regions of lepidopteran-specific insecticidal protein produced by *Bacillus thuringiensis*", *J. Biol. Chem*., 265(34):20923-20930, Dec. 1990.

Widner et al., "Two highly related insecticidal crystal proteins of *Bacillus thuringiensis* subsp. Kurstaki possess different host range specificities", *Journal of Bacteriology*, 171(2):965-974, Feb. 1, 1989.

Wong et al.,"*Arabidopsis thaliana* small subunit leader and transit peptide enhance the expression of *Bacillus thuringiensis* proteins in transgenic plants", *Plant Molecular Biology*, 20(1):81-93, Oct. 1, 1992.

Tu et al., "Expression and Function of a Hybrid Bt Toxin Gene in Transgenic Rice Conferring Resistance to Insect Pest"; Plant Biotechnol., vol. 15(4), pp. 195-203.

Office Action issued in Japanese Application No. 2008-529233, on Jul. 5, 2011.

* cited by examiner

*Primary Examiner* — Anne Kubelik

(74) *Attorney, Agent, or Firm* — SNR Denton US LLP; Timothy K. Ball, Esq.

(57) ABSTRACT

The present invention provides nucleotide sequences encoding an insecticidal protein exhibiting lepidopteran inhibitory activity, as well as a novel insecticidal protein referred to herein as a Cry1A.105 insecticide, transgenic plants expressing the insecticide, and methods for detecting the presence of the nucleotide sequences or the insecticide in a biological sample.

34 Claims, No Drawings

SEQUENCE LISTING

<160> NUMBER OF SEQ ID NOS: 8

<210> SEQ ID NO 1
<211> LENGTH: 3534
<212> TYPE: DNA
<213> ORGANISM: artificial
<220> FEATURE:
<223> OTHER INFORMATION: synthetic nucleotide sequence encoding Cry1A.105 amino acid sequence
<220> FEATURE:
<221> NAME/KEY: CDS
<222> LOCATION: (1)..(3534)

<400> SEQUENCE: 1

```
atg gac aac aac cca aac atc aac gaa tgc att cca tac aac tgc ttg      48
Met Asp Asn Asn Pro Asn Ile Asn Glu Cys Ile Pro Tyr Asn Cys Leu
1               5                   10                  15 agt aac cca gaa gtt gaa gta ctt ggt gga gaa cgc att gaa acc ggt      96
Ser Asn Pro Glu Val Glu Val Leu Gly Gly Glu Arg Ile Glu Thr Gly
            20                  25                  30 tac act ccc atc gac atc tcc ttg tcc ttg aca cag ttt ctg ctc agc     144
Tyr Thr Pro Ile Asp Ile Ser Leu Ser Leu Thr Gln Phe Leu Leu Ser
        35                  40                  45 gag ttc gtg cca ggt gct ggg ttc gtt ctc gga cta gtt gac atc atc     192
Glu Phe Val Pro Gly Ala Gly Phe Val Leu Gly Leu Val Asp Ile Ile
    50                  55                  60 tgg ggt atc ttt ggt cca tct caa tgg gat gca ttc ctg gtg caa att     240
Trp Gly Ile Phe Gly Pro Ser Gln Trp Asp Ala Phe Leu Val Gln Ile
65                  70                  75                  80 gag cag ttg atc aac cag agg atc gaa gag ttc gcc agg aac cag gcc     288
Glu Gln Leu Ile Asn Gln Arg Ile Glu Glu Phe Ala Arg Asn Gln Ala
                85                  90                  95 atc tct agg ttg gaa gga ttg agc aat ctc tac caa atc tat gca gag     336
Ile Ser Arg Leu Glu Gly Leu Ser Asn Leu Tyr Gln Ile Tyr Ala Glu
            100                 105                 110 agc ttc aga gag tgg gaa gcc gat cct act aac cca gct ctc cgc gag     384
Ser Phe Arg Glu Trp Glu Ala Asp Pro Thr Asn Pro Ala Leu Arg Glu
        115                 120                 125 gaa atg cgt att caa ttc aac gac atg aac agc gcc ttg acc aca gct     432
Glu Met Arg Ile Gln Phe Asn Asp Met Asn Ser Ala Leu Thr Thr Ala
    130                 135                 140 atc cca ttg ttc gca gtc cag aac tac caa gtt cct ctc ttg tcc gtg     480
Ile Pro Leu Phe Ala Val Gln Asn Tyr Gln Val Pro Leu Leu Ser Val
145                 150                 155                 160 tac gtt caa gca gct aat ctt cac ctc agc gtg ctt cga gac gtt agc     528
Tyr Val Gln Ala Ala Asn Leu His Leu Ser Val Leu Arg Asp Val Ser
                165                 170                 175 gtg ttt ggg caa agg tgg gga ttc gat gct gca acc atc aat agc cgt     576
Val Phe Gly Gln Arg Trp Gly Phe Asp Ala Ala Thr Ile Asn Ser Arg
            180                 185                 190 tac aac gac ctt act agg ctg att gga aac tac acc gac cac gct gtt     624
```

-continued

| | | |
|---|---|---|
| Tyr Asn Asp Leu Thr Arg Leu Ile Gly Asn Tyr Thr Asp His Ala Val<br>             195                      200                   205 | |
| cgt tgg tac aac act ggc ttg gag cgt gtc tgg ggt cct gat tct aga<br>Arg Trp Tyr Asn Thr Gly Leu Glu Arg Val Trp Gly Pro Asp Ser Arg<br>210                   215                   220 | 672 |
| gat tgg att aga tac aac cag ttc agg aga gaa ttg acc ctc aca gtt<br>Asp Trp Ile Arg Tyr Asn Gln Phe Arg Arg Glu Leu Thr Leu Thr Val<br>225                   230                   235                 240 | 720 |
| ttg gac att gtg tct ctc ttc ccg aac tat gac tcc aga acc tac cct<br>Leu Asp Ile Val Ser Leu Phe Pro Asn Tyr Asp Ser Arg Thr Tyr Pro<br>                       245                   250                 255 | 768 |
| atc cgt aca gtg tcc caa ctt acc aga gaa atc tat act aac cca gtt<br>Ile Arg Thr Val Ser Gln Leu Thr Arg Glu Ile Tyr Thr Asn Pro Val<br>             260                   265                   270 | 816 |
| ctt gag aac ttc gac ggt agc ttc cgt ggt tct gcc caa ggt atc gaa<br>Leu Glu Asn Phe Asp Gly Ser Phe Arg Gly Ser Ala Gln Gly Ile Glu<br>             275                   280                   285 | 864 |
| ggc tcc atc agg agc cca cac ttg atg gac atc ttg aac agc ata act<br>Gly Ser Ile Arg Ser Pro His Leu Met Asp Ile Leu Asn Ser Ile Thr<br>     290                   295                   300 | 912 |
| atc tac acc gat gct cac aga gga gag tat tac tgg tct gga cac cag<br>Ile Tyr Thr Asp Ala His Arg Gly Glu Tyr Tyr Trp Ser Gly His Gln<br>305                   310                   315                 320 | 960 |
| atc atg gcc tct cca gtt gga ttc agc ggg ccc gag ttt acc ttt cct<br>Ile Met Ala Ser Pro Val Gly Phe Ser Gly Pro Glu Phe Thr Phe Pro<br>                   325                   330                 335 | 1008 |
| ctc tat gga act atg gga aac gcc gct cca caa caa cgt atc gtt gct<br>Leu Tyr Gly Thr Met Gly Asn Ala Ala Pro Gln Gln Arg Ile Val Ala<br>                   340                   345                 350 | 1056 |
| caa cta ggt cag ggt gtc tac aga acc ttg tct tcc acc ttg tac aga<br>Gln Leu Gly Gln Gly Val Tyr Arg Thr Leu Ser Ser Thr Leu Tyr Arg<br>             355                   360                   365 | 1104 |
| aga ccc ttc aat atc ggt atc aac aac cag caa ctt tcc gtt ctt gac<br>Arg Pro Phe Asn Ile Gly Ile Asn Asn Gln Gln Leu Ser Val Leu Asp<br>     370                   375                   380 | 1152 |
| gga aca gag ttc gcc tat gga acc tct tct aac ttg cca tcc gct gtt<br>Gly Thr Glu Phe Ala Tyr Gly Thr Ser Ser Asn Leu Pro Ser Ala Val<br>385                   390                   395                 400 | 1200 |
| tac aga aag agc gga acc gtt gat tcc ttg gac gaa atc cca cca cag<br>Tyr Arg Lys Ser Gly Thr Val Asp Ser Leu Asp Glu Ile Pro Pro Gln<br>                   405                   410                 415 | 1248 |
| aac aac aat gtg cca ccc agg caa gga ttc tcc cac agg ttg agc cac<br>Asn Asn Asn Val Pro Pro Arg Gln Gly Phe Ser His Arg Leu Ser His<br>                   420                   425                 430 | 1296 |
| gtg tcc atg ttc cgt tcc gga ttc agc aac agt tcc gtg agc atc atc<br>Val Ser Met Phe Arg Ser Gly Phe Ser Asn Ser Ser Val Ser Ile Ile<br>             435                   440                   445 | 1344 |
| aga gct cct atg ttc tct tgg ata cac cgt agt gct gag ttc aac aac<br>Arg Ala Pro Met Phe Ser Trp Ile His Arg Ser Ala Glu Phe Asn Asn<br>     450                   455                   460 | 1392 |
| atc att gca tcc gac agc att act caa ata ccc ttg gtg aaa gca cat<br>Ile Ile Ala Ser Asp Ser Ile Thr Gln Ile Pro Leu Val Lys Ala His<br>465                   470                   475                 480 | 1440 |
| aca ctt cag tca ggt act act gtt gtc aga ggt cca ggg ttt aca gga<br>Thr Leu Gln Ser Gly Thr Thr Val Val Arg Gly Pro Gly Phe Thr Gly<br>                   485                   490                 495 | 1488 |
| gga gac att ctt cgt cgc aca agt gga gga ccc ttt gct tac act att<br>Gly Asp Ile Leu Arg Arg Thr Ser Gly Gly Pro Phe Ala Tyr Thr Ile<br>             500                   505                   510 | 1536 |
| gtt aac atc aat ggc caa ttg ccc caa agg tat cgt gca aga atc cgc | 1584 |

-continued

| | | | | | | | | | | | | | |
|---|---|---|---|---|---|---|---|---|---|---|---|---|---|
| Val | Asn | Ile | Asn | Gly | Gln | Leu | Pro | Gln | Arg | Tyr | Arg | Ala | Arg | Ile | Arg |
| | | 515 | | | | 520 | | | | 525 | | | |

| tat | gcc | tct | act | aca | aat | ctc | agg | atc | tac | gtg | act | gtt | gca | ggt | gaa | 1632 |
|---|---|---|---|---|---|---|---|---|---|---|---|---|---|---|---|---|
| Tyr | Ala | Ser | Thr | Thr | Asn | Leu | Arg | Ile | Tyr | Val | Thr | Val | Ala | Gly | Glu | |
| 530 | | | | | 535 | | | | | 540 | | | | | | |

| agg | atc | ttt | gct | ggt | cag | ttc | aac | aag | act | atg | gat | acc | ggt | gac | cct | 1680 |
|---|---|---|---|---|---|---|---|---|---|---|---|---|---|---|---|---|
| Arg | Ile | Phe | Ala | Gly | Gln | Phe | Asn | Lys | Thr | Met | Asp | Thr | Gly | Asp | Pro | |
| 545 | | | | 550 | | | | | 555 | | | | | 560 | | |

| ttg | aca | ttc | caa | tct | ttt | agc | tac | gca | act | atc | aac | aca | gct | ttt | aca | 1728 |
|---|---|---|---|---|---|---|---|---|---|---|---|---|---|---|---|---|
| Leu | Thr | Phe | Gln | Ser | Phe | Ser | Tyr | Ala | Thr | Ile | Asn | Thr | Ala | Phe | Thr | |
| | | | | 565 | | | | | 570 | | | | | 575 | | |

| ttc | cca | atg | agc | cag | agt | agc | ttc | aca | gta | ggt | gct | gac | act | ttc | agc | 1776 |
|---|---|---|---|---|---|---|---|---|---|---|---|---|---|---|---|---|
| Phe | Pro | Met | Ser | Gln | Ser | Ser | Phe | Thr | Val | Gly | Ala | Asp | Thr | Phe | Ser | |
| | | | 580 | | | | | 585 | | | | | 590 | | | |

| tca | ggg | aat | gaa | gtt | tac | atc | gac | agg | ttt | gaa | ttg | att | cca | gtt | act | 1824 |
|---|---|---|---|---|---|---|---|---|---|---|---|---|---|---|---|---|
| Ser | Gly | Asn | Glu | Val | Tyr | Ile | Asp | Arg | Phe | Glu | Leu | Ile | Pro | Val | Thr | |
| | | | 595 | | | | | 600 | | | | | 605 | | | |

| gca | acc | ctc | gag | gct | gag | tac | aac | ctt | gag | aga | gcc | cag | aag | gct | gtg | 1872 |
|---|---|---|---|---|---|---|---|---|---|---|---|---|---|---|---|---|
| Ala | Thr | Leu | Glu | Ala | Glu | Tyr | Asn | Leu | Glu | Arg | Ala | Gln | Lys | Ala | Val | |
| | 610 | | | | | 615 | | | | | 620 | | | | | |

| aac | gcc | ctc | ttt | acc | tcc | acc | aat | cag | ctt | ggc | ttg | aaa | act | aac | gtt | 1920 |
|---|---|---|---|---|---|---|---|---|---|---|---|---|---|---|---|---|
| Asn | Ala | Leu | Phe | Thr | Ser | Thr | Asn | Gln | Leu | Gly | Leu | Lys | Thr | Asn | Val | |
| 625 | | | | | 630 | | | | | 635 | | | | | 640 | |

| act | gac | tat | cac | att | gac | caa | gtg | tcc | aac | ttg | gtc | acc | tac | ctt | agc | 1968 |
|---|---|---|---|---|---|---|---|---|---|---|---|---|---|---|---|---|
| Thr | Asp | Tyr | His | Ile | Asp | Gln | Val | Ser | Asn | Leu | Val | Thr | Tyr | Leu | Ser | |
| | | | | 645 | | | | | 650 | | | | | 655 | | |

| gat | gag | ttc | tgc | ctc | gac | gag | aag | cgt | gaa | ctc | tcc | gag | aaa | gtt | aaa | 2016 |
|---|---|---|---|---|---|---|---|---|---|---|---|---|---|---|---|---|
| Asp | Glu | Phe | Cys | Leu | Asp | Glu | Lys | Arg | Glu | Leu | Ser | Glu | Lys | Val | Lys | |
| | | | 660 | | | | | 665 | | | | | 670 | | | |

| cac | gcc | aag | cgt | ctc | agc | gac | gag | agg | aat | ctc | ttg | caa | gac | tcc | aac | 2064 |
|---|---|---|---|---|---|---|---|---|---|---|---|---|---|---|---|---|
| His | Ala | Lys | Arg | Leu | Ser | Asp | Glu | Arg | Asn | Leu | Leu | Gln | Asp | Ser | Asn | |
| | | 675 | | | | | 680 | | | | | 685 | | | | |

| ttc | aaa | gac | atc | aac | agg | cag | cca | gaa | cgt | ggt | tgg | ggt | gga | agc | acc | 2112 |
|---|---|---|---|---|---|---|---|---|---|---|---|---|---|---|---|---|
| Phe | Lys | Asp | Ile | Asn | Arg | Gln | Pro | Glu | Arg | Gly | Trp | Gly | Gly | Ser | Thr | |
| 690 | | | | | 695 | | | | | 700 | | | | | | |

| ggg | atc | acc | atc | caa | gga | ggc | gac | gat | gtg | ttc | aag | gag | aac | tac | gtc | 2160 |
|---|---|---|---|---|---|---|---|---|---|---|---|---|---|---|---|---|
| Gly | Ile | Thr | Ile | Gln | Gly | Gly | Asp | Asp | Val | Phe | Lys | Glu | Asn | Tyr | Val | |
| 705 | | | | 710 | | | | | 715 | | | | | 720 | | |

| acc | ctc | tcc | gga | act | ttc | gac | gag | tgc | tac | cct | acc | tac | ttg | tac | cag | 2208 |
|---|---|---|---|---|---|---|---|---|---|---|---|---|---|---|---|---|
| Thr | Leu | Ser | Gly | Thr | Phe | Asp | Glu | Cys | Tyr | Pro | Thr | Tyr | Leu | Tyr | Gln | |
| | | | | 725 | | | | | 730 | | | | | 735 | | |

| aag | atc | gat | gag | tcc | aaa | ctc | aaa | gcc | ttc | acc | agg | tat | caa | ctt | aga | 2256 |
|---|---|---|---|---|---|---|---|---|---|---|---|---|---|---|---|---|
| Lys | Ile | Asp | Glu | Ser | Lys | Leu | Lys | Ala | Phe | Thr | Arg | Tyr | Gln | Leu | Arg | |
| | | | 740 | | | | | 745 | | | | | 750 | | | |

| ggc | tac | atc | gaa | gac | agc | caa | gac | ctt | gaa | atc | tac | tcg | atc | agg | tac | 2304 |
|---|---|---|---|---|---|---|---|---|---|---|---|---|---|---|---|---|
| Gly | Tyr | Ile | Glu | Asp | Ser | Gln | Asp | Leu | Glu | Ile | Tyr | Ser | Ile | Arg | Tyr | |
| | | 755 | | | | | 760 | | | | | 765 | | | | |

| aat | gcc | aag | cac | gag | acc | gtg | aat | gtc | cca | ggt | act | ggt | tcc | ctc | tgg | 2352 |
|---|---|---|---|---|---|---|---|---|---|---|---|---|---|---|---|---|
| Asn | Ala | Lys | His | Glu | Thr | Val | Asn | Val | Pro | Gly | Thr | Gly | Ser | Leu | Trp | |
| | 770 | | | | | 775 | | | | | 780 | | | | | |

| cca | ctt | tct | gcc | caa | tct | ccc | att | ggg | aag | tgt | gga | gag | cct | aac | aga | 2400 |
|---|---|---|---|---|---|---|---|---|---|---|---|---|---|---|---|---|
| Pro | Leu | Ser | Ala | Gln | Ser | Pro | Ile | Gly | Lys | Cys | Gly | Glu | Pro | Asn | Arg | |
| 785 | | | | 790 | | | | | 795 | | | | | 800 | | |

| tgc | gct | cca | cac | ctt | gag | tgg | aat | cct | gac | ttg | gac | tgc | tcc | tgc | agg | 2448 |
|---|---|---|---|---|---|---|---|---|---|---|---|---|---|---|---|---|
| Cys | Ala | Pro | His | Leu | Glu | Trp | Asn | Pro | Asp | Leu | Asp | Cys | Ser | Cys | Arg | |
| | | | | 805 | | | | | 810 | | | | | 815 | | |

| gat | ggc | gag | aag | tgt | gcc | cac | cat | tct | cat | cac | ttc | tcc | ttg | gac | atc | 2496 |
|---|---|---|---|---|---|---|---|---|---|---|---|---|---|---|---|---|
| Asp | Gly | Glu | Lys | Cys | Ala | His | His | Ser | His | His | Phe | Ser | Leu | Asp | Ile | |
| | | | 820 | | | | | 825 | | | | | 830 | | | |

| gat | gtg | gga | tgt | act | gac | ctg | aat | gag | gac | ctc | gga | gtc | tgg | gtc | atc | 2544 |

```
        Asp Val Gly Cys Thr Asp Leu Asn Glu Asp Leu Gly Val Trp Val Ile
            835                 840                 845 ttc aag atc aag acc caa gac gga cac gca aga ctt ggc aac ctt gag        2592
Phe Lys Ile Lys Thr Gln Asp Gly His Ala Arg Leu Gly Asn Leu Glu
850                 855                 860 ttt ctc gaa gag aaa cca ttg gtc ggt gaa gct ctc gct cgt gtg aag        2640
Phe Leu Glu Glu Lys Pro Leu Val Gly Glu Ala Leu Ala Arg Val Lys
865                 870                 875                 880 aga gca gag aag aag tgg agg gac aaa cgt gag aaa ctc gaa tgg gaa        2688
Arg Ala Glu Lys Lys Trp Arg Asp Lys Arg Glu Lys Leu Glu Trp Glu
                885                 890                 895 act aac atc gtt tac aag gag gcc aaa gag tcc gtg gat gct ttg ttc        2736
Thr Asn Ile Val Tyr Lys Glu Ala Lys Glu Ser Val Asp Ala Leu Phe
        900                 905                 910 gtg aac tcc caa tat gat cag ttg caa gcc gac acc aac atc gcc atg        2784
Val Asn Ser Gln Tyr Asp Gln Leu Gln Ala Asp Thr Asn Ile Ala Met
            915                 920                 925 atc cac gcc gca gac aaa cgt gtg cac agc att cgt gag gct tac ttg        2832
Ile His Ala Ala Asp Lys Arg Val His Ser Ile Arg Glu Ala Tyr Leu
                930                 935                 940 cct gag ttg tcc gtg atc cct ggt gtg aac gct gcc atc ttc gag gaa        2880
Pro Glu Leu Ser Val Ile Pro Gly Val Asn Ala Ala Ile Phe Glu Glu
945                 950                 955                 960 ctt gag gga cgt atc ttt acc gca ttc tcc ttg tac gat gcc aga aac        2928
Leu Glu Gly Arg Ile Phe Thr Ala Phe Ser Leu Tyr Asp Ala Arg Asn
                965                 970                 975 gtc atc aag aac ggt gac ttc aac aat ggc ctc agc tgc tgg aat gtg        2976
Val Ile Lys Asn Gly Asp Phe Asn Asn Gly Leu Ser Cys Trp Asn Val
            980                 985                 990 aaa ggt cat gtg gac gtg gag gaa cag aac aat cag cgt tcc gtc ctg        3024
Lys Gly His Val Asp Val Glu Glu Gln Asn Asn Gln Arg Ser Val Leu
                995                 1000                1005 gtt gtg cct gag tgg gaa gct gaa gtg tcc caa gag gtt aga gtc             3069
Val Val Pro Glu Trp Glu Ala Glu Val Ser Gln Glu Val Arg Val
        1010                1015                1020 tgt cca ggt aga ggc tac att ctc cgt gtg acc gct tac aag gag             3114
Cys Pro Gly Arg Gly Tyr Ile Leu Arg Val Thr Ala Tyr Lys Glu
    1025                1030                1035 gga tac ggt gag ggt tgc gtg acc atc cac gag atc gag aac aac             3159
Gly Tyr Gly Glu Gly Cys Val Thr Ile His Glu Ile Glu Asn Asn
    1040                1045                1050 acc gac gag ctt aag ttc tcc aac tgc gtc gag gaa gaa atc tat             3204
Thr Asp Glu Leu Lys Phe Ser Asn Cys Val Glu Glu Glu Ile Tyr
    1055                1060                1065 ccc aac aac acc gtt act tgc aac gac tac act gtg aat cag gaa             3249
Pro Asn Asn Thr Val Thr Cys Asn Asp Tyr Thr Val Asn Gln Glu
    1070                1075                1080 gag tac gga ggt gcc tac act agc cgt aac aga ggt tac aac gaa             3294
Glu Tyr Gly Gly Ala Tyr Thr Ser Arg Asn Arg Gly Tyr Asn Glu
    1085                1090                1095 gct cct tcc gtt cct gct gac tat gcc tcc gtg tac gag gag aaa             3339
Ala Pro Ser Val Pro Ala Asp Tyr Ala Ser Val Tyr Glu Glu Lys
    1100                1105                1110 tcc tac aca gat ggc aga cgt gag aac cct tgc gag ttc aac aga             3384
Ser Tyr Thr Asp Gly Arg Arg Glu Asn Pro Cys Glu Phe Asn Arg
    1115                1120                1125 ggt tac agg gac tac aca cca ctt cca gtt ggc tat gtt acc aag             3429
Gly Tyr Arg Asp Tyr Thr Pro Leu Pro Val Gly Tyr Val Thr Lys
    1130                1135                1140 gag ctt gag tac ttt cct gag acc gac aaa gtg tgg atc gag atc             3474
```

```
                                                   -continued

Glu Leu Glu Tyr Phe Pro Glu Thr Asp Lys Val Trp Ile Glu Ile
    1145                1150                1155 ggt gaa acc gag gga acc ttc atc gtg gac agc gtg gag ctt ctc      3519
Gly Glu Thr Glu Gly Thr Phe Ile Val Asp Ser Val Glu Leu Leu
    1160                1165                1170 ttg atg gag gaa taa                                              3534
Leu Met Glu Glu
        1175

<210> SEQ ID NO 2
<211> LENGTH: 1177
<212> TYPE: PRT
<213> ORGANISM: artificial
<220> FEATURE:
<223> OTHER INFORMATION: Synthetic Construct

<400> SEQUENCE: 2

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320
```

```
Ile Met Ala Ser Pro Val Gly Phe Ser Gly Pro Glu Phe Thr Phe Pro
            325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
            405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
450                 455                 460
Ile Ile Ala Ser Asp Ser Ile Thr Gln Ile Pro Leu Val Lys Ala His
465                 470                 475                 480
Thr Leu Gln Ser Gly Thr Thr Val Val Arg Gly Pro Gly Phe Thr Gly
            485                 490                 495
Gly Asp Ile Leu Arg Arg Thr Ser Gly Gly Pro Phe Ala Tyr Thr Ile
            500                 505                 510
Val Asn Ile Asn Gly Gln Leu Pro Gln Arg Tyr Arg Ala Arg Ile Arg
            515                 520                 525
Tyr Ala Ser Thr Thr Asn Leu Arg Ile Tyr Val Thr Val Ala Gly Glu
530                 535                 540
Arg Ile Phe Ala Gly Gln Phe Asn Lys Thr Met Asp Thr Gly Asp Pro
545                 550                 555                 560
Leu Thr Phe Gln Ser Phe Ser Tyr Ala Thr Ile Asn Thr Ala Phe Thr
            565                 570                 575
Phe Pro Met Ser Gln Ser Ser Phe Thr Val Gly Ala Asp Thr Phe Ser
            580                 585                 590
Ser Gly Asn Glu Val Tyr Ile Asp Arg Phe Glu Leu Ile Pro Val Thr
            595                 600                 605
Ala Thr Leu Glu Ala Glu Tyr Asn Leu Glu Arg Ala Gln Lys Ala Val
            610                 615                 620
Asn Ala Leu Phe Thr Ser Thr Asn Gln Leu Gly Leu Lys Thr Asn Val
625                 630                 635                 640
Thr Asp Tyr His Ile Asp Gln Val Ser Asn Leu Val Thr Tyr Leu Ser
            645                 650                 655
Asp Glu Phe Cys Leu Asp Glu Lys Arg Glu Leu Ser Glu Lys Val Lys
            660                 665                 670
His Ala Lys Arg Leu Ser Asp Glu Arg Asn Leu Leu Gln Asp Ser Asn
            675                 680                 685
Phe Lys Asp Ile Asn Arg Gln Pro Glu Arg Gly Trp Gly Gly Ser Thr
690                 695                 700
Gly Ile Thr Ile Gln Gly Gly Asp Asp Val Phe Lys Glu Asn Tyr Val
705                 710                 715                 720
Thr Leu Ser Gly Thr Phe Asp Glu Cys Tyr Pro Thr Tyr Leu Tyr Gln
            725                 730                 735
Lys Ile Asp Glu Ser Lys Leu Lys Ala Phe Thr Arg Tyr Gln Leu Arg
```

-continued

```
                    740             745                 750
Gly Tyr Ile Glu Asp Ser Gln Asp Leu Glu Ile Tyr Ser Ile Arg Tyr
            755                 760             765
Asn Ala Lys His Glu Thr Val Asn Val Pro Gly Thr Gly Ser Leu Trp
    770                 775                 780
Pro Leu Ser Ala Gln Ser Pro Ile Gly Lys Cys Gly Glu Pro Asn Arg
785                 790                 795                 800
Cys Ala Pro His Leu Glu Trp Asn Pro Asp Leu Asp Cys Ser Cys Arg
                805                 810                 815
Asp Gly Glu Lys Cys Ala His His Ser His His Phe Ser Leu Asp Ile
            820                 825                 830
Asp Val Gly Cys Thr Asp Leu Asn Glu Asp Leu Gly Val Trp Val Ile
            835                 840                 845
Phe Lys Ile Lys Thr Gln Asp Gly His Ala Arg Leu Gly Asn Leu Glu
            850                 855                 860
Phe Leu Glu Glu Lys Pro Leu Val Gly Glu Ala Leu Ala Arg Val Lys
865                 870                 875                 880
Arg Ala Glu Lys Lys Trp Arg Asp Lys Arg Glu Lys Leu Glu Trp Glu
                885                 890                 895
Thr Asn Ile Val Tyr Lys Glu Ala Lys Glu Ser Val Asp Ala Leu Phe
                900                 905                 910
Val Asn Ser Gln Tyr Asp Gln Leu Gln Ala Asp Thr Asn Ile Ala Met
            915                 920                 925
Ile His Ala Ala Asp Lys Arg Val His Ser Ile Arg Glu Ala Tyr Leu
            930                 935                 940
Pro Glu Leu Ser Val Ile Pro Gly Val Asn Ala Ala Ile Phe Glu Glu
945                 950                 955                 960
Leu Glu Gly Arg Ile Phe Thr Ala Phe Ser Leu Tyr Asp Ala Arg Asn
                965                 970                 975
Val Ile Lys Asn Gly Asp Phe Asn Asn Gly Leu Ser Cys Trp Asn Val
            980                 985                 990
Lys Gly His Val Asp Val Glu Glu Gln Asn Asn Gln Arg Ser Val Leu
            995                 1000                1005
Val Val Pro Glu Trp Glu Ala Glu Val Ser Gln Glu Val Arg Val
    1010                1015                1020
Cys Pro Gly Arg Gly Tyr Ile Leu Arg Val Thr Ala Tyr Lys Glu
    1025                1030                1035
Gly Tyr Gly Glu Gly Cys Val Thr Ile His Glu Ile Glu Asn Asn
    1040                1045                1050
Thr Asp Glu Leu Lys Phe Ser Asn Cys Val Glu Glu Glu Ile Tyr
    1055                1060                1065
Pro Asn Asn Thr Val Thr Cys Asn Asp Tyr Thr Val Asn Gln Glu
    1070                1075                1080
Glu Tyr Gly Gly Ala Tyr Thr Ser Arg Asn Arg Gly Tyr Asn Glu
    1085                1090                1095
Ala Pro Ser Val Pro Ala Asp Tyr Ala Ser Val Tyr Glu Glu Lys
    1100                1105                1110
Ser Tyr Thr Asp Gly Arg Arg Glu Asn Pro Cys Glu Phe Asn Arg
    1115                1120                1125
Gly Tyr Arg Asp Tyr Thr Pro Leu Pro Val Gly Tyr Val Thr Lys
    1130                1135                1140
Glu Leu Glu Tyr Phe Pro Glu Thr Asp Lys Val Trp Ile Glu Ile
    1145                1150                1155
```

```
                                      Gly Glu Thr Glu Gly Thr Phe Ile Val Asp Ser Val Glu Leu Leu
                                          1160                1165                1170

Leu Met Glu Glu
                                          1175

<210> SEQ ID NO 3
<211> LENGTH: 3534
<212> TYPE: DNA
<213> ORGANISM: artificial
<220> FEATURE:
<223> OTHER INFORMATION: synthetic nucleotide sequence encoding
      Cry1A.105 amino acid sequence
<220> FEATURE:
<221> NAME/KEY: CDS
<222> LOCATION: (1)..(3534)

<400> SEQUENCE: 3 atg gac aac aac cca aac atc aac gag tgc atc ccg tac aac tgc ctc        48
Met Asp Asn Asn Pro Asn Ile Asn Glu Cys Ile Pro Tyr Asn Cys Leu
1               5                  10                  15 agc aac cct gag gtc gag gtg ctc ggc ggt gag cgc atc gag acc ggt        96
Ser Asn Pro Glu Val Glu Val Leu Gly Gly Glu Arg Ile Glu Thr Gly
            20                  25                  30 tac acc ccc atc gac atc tcc ctc tcc ctc acg cag ttc ctg ctc agc       144
Tyr Thr Pro Ile Asp Ile Ser Leu Ser Leu Thr Gln Phe Leu Leu Ser
        35                  40                  45 gag ttc gtg cca ggc gct ggc ttc gtc ctg ggc ctc gtg gac atc atc       192
Glu Phe Val Pro Gly Ala Gly Phe Val Leu Gly Leu Val Asp Ile Ile
    50                  55                  60 tgg ggc atc ttt ggc ccc tcc cag tgg gac gcc ttc ctg gtg caa atc       240
Trp Gly Ile Phe Gly Pro Ser Gln Trp Asp Ala Phe Leu Val Gln Ile
65                  70                  75                  80 gag cag ctc atc aac cag agg atc gag gag ttc gcc agg aac cag gcc       288
Glu Gln Leu Ile Asn Gln Arg Ile Glu Glu Phe Ala Arg Asn Gln Ala
                85                  90                  95 atc agc cgc ctg gag ggc ctc agc aac ctc tac caa atc tac gct gag       336
Ile Ser Arg Leu Glu Gly Leu Ser Asn Leu Tyr Gln Ile Tyr Ala Glu
            100                 105                 110 agc ttc cgc gag tgg gag gcc gac ccc act aac cca gct ctc cgc gag       384
Ser Phe Arg Glu Trp Glu Ala Asp Pro Thr Asn Pro Ala Leu Arg Glu
        115                 120                 125 gag atg cgc atc cag ttc aac gac atg aac agc gcc ctg acc acc gcc       432
Glu Met Arg Ile Gln Phe Asn Asp Met Asn Ser Ala Leu Thr Thr Ala
    130                 135                 140 atc cca ctc ttc gcc gtc cag aac tac caa gtc ccg ctc ctg tcc gtg       480
Ile Pro Leu Phe Ala Val Gln Asn Tyr Gln Val Pro Leu Leu Ser Val
145                 150                 155                 160 tac gtc cag gcc gcc aac ctg cac ctc agc gtg ctg agg gac gtc agc       528
Tyr Val Gln Ala Ala Asn Leu His Leu Ser Val Leu Arg Asp Val Ser
                165                 170                 175 gtg ttt ggc cag agg tgg ggc ttc gac gcc gcc acc atc aac agc cgc       576
Val Phe Gly Gln Arg Trp Gly Phe Asp Ala Ala Thr Ile Asn Ser Arg
            180                 185                 190 tac aac gac ctc acc agg ctg atc ggc aac tac acc gac cac gct gtc       624
Tyr Asn Asp Leu Thr Arg Leu Ile Gly Asn Tyr Thr Asp His Ala Val
        195                 200                 205 cgc tgg tac aac act ggc ctg gag cgc gtc tgg ggc cct gat tct aga       672
Arg Trp Tyr Asn Thr Gly Leu Glu Arg Val Trp Gly Pro Asp Ser Arg
    210                 215                 220 gac tgg att cgc tac aac cag ttc agg cgc gag ctg acc ctc acc gtc       720
Asp Trp Ile Arg Tyr Asn Gln Phe Arg Arg Glu Leu Thr Leu Thr Val
225                 230                 235                 240
```

| | | |
|---|---|---|
| ctg gac att gtg tcc ctc ttc ccg aac tac gac tcc cgc acc tac ccg<br>Leu Asp Ile Val Ser Leu Phe Pro Asn Tyr Asp Ser Arg Thr Tyr Pro<br>245                    250                  255 | 768 |
| atc cgc acc gtg tcc caa ctg acc cgc gaa atc tac acc aac ccc gtc<br>Ile Arg Thr Val Ser Gln Leu Thr Arg Glu Ile Tyr Thr Asn Pro Val<br>        260                  265                  270 | 816 |
| ctg gag aac ttc gac ggt agc ttc agg ggc agc gcc cag ggc atc gag<br>Leu Glu Asn Phe Asp Gly Ser Phe Arg Gly Ser Ala Gln Gly Ile Glu<br>             275                  280                  285 | 864 |
| ggc tcc atc agg agc cca cac ctg atg gac atc ctc aac agc atc act<br>Gly Ser Ile Arg Ser Pro His Leu Met Asp Ile Leu Asn Ser Ile Thr<br>290                    295                  300 | 912 |
| atc tac acc gat gcc cac cgc ggc gag tac tac tgg tcc ggc cac cag<br>Ile Tyr Thr Asp Ala His Arg Gly Glu Tyr Tyr Trp Ser Gly His Gln<br>305                    310                  315                  320 | 960 |
| atc atg gcc tcc ccg gtc ggc ttc agc ggc ccc gag ttt acc ttt cct<br>Ile Met Ala Ser Pro Val Gly Phe Ser Gly Pro Glu Phe Thr Phe Pro<br>                    325                  330                  335 | 1008 |
| ctc tac ggc acg atg ggc aac gcc gct cca caa caa cgc atc gtc gct<br>Leu Tyr Gly Thr Met Gly Asn Ala Ala Pro Gln Gln Arg Ile Val Ala<br>340                    345                  350 | 1056 |
| cag ctg ggc cag ggc gtc tac cgc acc ctg agc tcc acc ctg tac cgc<br>Gln Leu Gly Gln Gly Val Tyr Arg Thr Leu Ser Ser Thr Leu Tyr Arg<br>        355                  360                  365 | 1104 |
| agg ccc ttc aac atc ggt atc aac aac cag cag ctg tcc gtc ctg gat<br>Arg Pro Phe Asn Ile Gly Ile Asn Asn Gln Gln Leu Ser Val Leu Asp<br>370                    375                  380 | 1152 |
| ggc act gag ttc gcc tac ggc acc tcc tcc aac ctg ccc tcc gct gtc<br>Gly Thr Glu Phe Ala Tyr Gly Thr Ser Ser Asn Leu Pro Ser Ala Val<br>385                    390                  395                  400 | 1200 |
| tac cgc aag agc ggc acg gtg gat tcc ctg gac gag atc cca cca cag<br>Tyr Arg Lys Ser Gly Thr Val Asp Ser Leu Asp Glu Ile Pro Pro Gln<br>                    405                  410                  415 | 1248 |
| aac aac aat gtg ccc ccc agg cag ggt ttt tcc cac agg ctc agc cac<br>Asn Asn Asn Val Pro Pro Arg Gln Gly Phe Ser His Arg Leu Ser His<br>                420                  425                  430 | 1296 |
| gtg tcc atg ttc cgc tcc ggc ttc agc aac tcg tcc gtg agc atc atc<br>Val Ser Met Phe Arg Ser Gly Phe Ser Asn Ser Ser Val Ser Ile Ile<br>        435                  440                  445 | 1344 |
| aga gct cct atg ttc tct tgg ata cac cgt agt gct gag ttc aac aac<br>Arg Ala Pro Met Phe Ser Trp Ile His Arg Ser Ala Glu Phe Asn Asn<br>450                    455                  460 | 1392 |
| atc att gca tcc gac agc att act caa ata ccc ttg gtg aaa gca cat<br>Ile Ile Ala Ser Asp Ser Ile Thr Gln Ile Pro Leu Val Lys Ala His<br>465                    470                  475                  480 | 1440 |
| aca ctt cag tca ggt act act gtt gtc aga ggt cca ggg ttt aca gga<br>Thr Leu Gln Ser Gly Thr Thr Val Val Arg Gly Pro Gly Phe Thr Gly<br>                    485                  490                  495 | 1488 |
| gga gac att ctt cgt cgc aca agt gga gga ccc ttt gct tac act att<br>Gly Asp Ile Leu Arg Arg Thr Ser Gly Gly Pro Phe Ala Tyr Thr Ile<br>500                    505                  510 | 1536 |
| gtt aac atc aat ggc caa ttg ccc caa agg tat cgt gca aga atc cgc<br>Val Asn Ile Asn Gly Gln Leu Pro Gln Arg Tyr Arg Ala Arg Ile Arg<br>515                    520                  525 | 1584 |
| tat gcc tct act aca aat ctc agg atc tac gtg act gtt gca ggt gaa<br>Tyr Ala Ser Thr Thr Asn Leu Arg Ile Tyr Val Thr Val Ala Gly Glu<br>        530                  535                  540 | 1632 |
| agg atc ttt gct ggt cag ttc aac aag act atg gat acc ggt gac cct<br>Arg Ile Phe Ala Gly Gln Phe Asn Lys Thr Met Asp Thr Gly Asp Pro<br>545                    550                  555                  560 | 1680 |

| | |
|---|---|
| ttg aca ttc caa tct ttt agc tac gca act atc aac aca gct ttt aca<br>Leu Thr Phe Gln Ser Phe Ser Tyr Ala Thr Ile Asn Thr Ala Phe Thr<br>                565                    570                  575 | 1728 |
| ttc cca atg agc cag agt agc ttc aca gta ggt gct gac act ttc agc<br>Phe Pro Met Ser Gln Ser Ser Phe Thr Val Gly Ala Asp Thr Phe Ser<br>            580                    585                    590 | 1776 |
| tca ggg aat gaa gtt tac atc gac agg ttt gaa ttg att cca gtt act<br>Ser Gly Asn Glu Val Tyr Ile Asp Arg Phe Glu Leu Ile Pro Val Thr<br>               595                    600                    605 | 1824 |
| gca acc ctc gag gct gag tac aac ctt gag aga gcc cag aag gct gtg<br>Ala Thr Leu Glu Ala Glu Tyr Asn Leu Glu Arg Ala Gln Lys Ala Val<br>            610                    615                    620 | 1872 |
| aac gcc ctc ttt acc tcc acc aat cag ctt ggc ttg aaa act aac gtt<br>Asn Ala Leu Phe Thr Ser Thr Asn Gln Leu Gly Leu Lys Thr Asn Val<br>625                    630                    635                  640 | 1920 |
| act gac tat cac att gac caa gtg tcc aac ttg gtc acc tac ctt agc<br>Thr Asp Tyr His Ile Asp Gln Val Ser Asn Leu Val Thr Tyr Leu Ser<br>                        645                    650                    655 | 1968 |
| gat gag ttc tgc ctc gac gag aag cgt gaa ctc tcc gag aaa gtt aaa<br>Asp Glu Phe Cys Leu Asp Glu Lys Arg Glu Leu Ser Glu Lys Val Lys<br>            660                    665                    670 | 2016 |
| cac gcc aag cgt ctc agc gac gag agg aat ctc ttg caa gac tcc aac<br>His Ala Lys Arg Leu Ser Asp Glu Arg Asn Leu Leu Gln Asp Ser Asn<br>               675                    680                    685 | 2064 |
| ttc aaa gac atc aac agg cag cca gaa cgt ggt tgg ggt gga agc acc<br>Phe Lys Asp Ile Asn Arg Gln Pro Glu Arg Gly Trp Gly Gly Ser Thr<br>            690                    695                    700 | 2112 |
| ggg atc acc atc caa gga ggc gac gat gtg ttc aag gag aac tac gtc<br>Gly Ile Thr Ile Gln Gly Gly Asp Asp Val Phe Lys Glu Asn Tyr Val<br>705                    710                    715                  720 | 2160 |
| acc ctc tcc gga act ttc gac gag tgc tac cct acc tac ttg tac cag<br>Thr Leu Ser Gly Thr Phe Asp Glu Cys Tyr Pro Thr Tyr Leu Tyr Gln<br>                        725                    730                    735 | 2208 |
| aag atc gat gag tcc aaa ctc aaa gcc ttc acc agg tat caa ctt aga<br>Lys Ile Asp Glu Ser Lys Leu Lys Ala Phe Thr Arg Tyr Gln Leu Arg<br>            740                    745                    750 | 2256 |
| ggc tac atc gaa gac agc caa gac ctt gaa atc tac tcg atc agg tac<br>Gly Tyr Ile Glu Asp Ser Gln Asp Leu Glu Ile Tyr Ser Ile Arg Tyr<br>               755                    760                    765 | 2304 |
| aat gcc aag cac gag acc gtg aat gtc cca ggt act ggt tcc ctc tgg<br>Asn Ala Lys His Glu Thr Val Asn Val Pro Gly Thr Gly Ser Leu Trp<br>            770                    775                    780 | 2352 |
| cca ctt tct gcc caa tct ccc att ggg aag tgt gga gag cct aac aga<br>Pro Leu Ser Ala Gln Ser Pro Ile Gly Lys Cys Gly Glu Pro Asn Arg<br>785                    790                    795                  800 | 2400 |
| tgc gct cca cac ctt gag tgg aat cct gac ttg gac tgc tcc tgc agg<br>Cys Ala Pro His Leu Glu Trp Asn Pro Asp Leu Asp Cys Ser Cys Arg<br>               805                    810                    815 | 2448 |
| gat ggc gag aag tgt gcc cac cat tct cat cac ttc tcc ttg gac atc<br>Asp Gly Glu Lys Cys Ala His His Ser His His Phe Ser Leu Asp Ile<br>            820                    825                    830 | 2496 |
| gat gtg gga tgt act gac ctg aat gag gac ctc gga gtc tgg gtc atc<br>Asp Val Gly Cys Thr Asp Leu Asn Glu Asp Leu Gly Val Trp Val Ile<br>               835                    840                    845 | 2544 |
| ttc aag atc aag acc caa gac gga cac gca aga ctt ggc aac ctt gag<br>Phe Lys Ile Lys Thr Gln Asp Gly His Ala Arg Leu Gly Asn Leu Glu<br>850                    855                    860 | 2592 |
| ttt ctc gaa gag aaa cca ttg gtc ggt gaa gct ctc gct cgt gtg aag<br>Phe Leu Glu Glu Lys Pro Leu Val Gly Glu Ala Leu Ala Arg Val Lys<br>865                    870                    875                  880 | 2640 |

-continued

| | | |
|---|---|---|
| aga gca gag aag aag tgg agg gac aaa cgt gag aaa ctc gaa tgg gaa<br>Arg Ala Glu Lys Lys Trp Arg Asp Lys Arg Glu Lys Leu Glu Trp Glu<br>                885                        890                    895 | 2688 |
| act aac atc gtt tac aag gag gcc aaa gag tcc gtg gat gct ttg ttc<br>Thr Asn Ile Val Tyr Lys Glu Ala Lys Glu Ser Val Asp Ala Leu Phe<br>         900                      905                      910 | 2736 |
| gtg aac tcc caa tat gat cag ttg caa gcc gac acc aac atc gcc atg<br>Val Asn Ser Gln Tyr Asp Gln Leu Gln Ala Asp Thr Asn Ile Ala Met<br>         915                      920                      925 | 2784 |
| atc cac gcc gca gac aaa cgt gtg cac agc att cgt gag gct tac ttg<br>Ile His Ala Ala Asp Lys Arg Val His Ser Ile Arg Glu Ala Tyr Leu<br>         930                      935                      940 | 2832 |
| cct gag ttg tcc gtg atc cct ggt gtg aac gct gcc atc ttc gag gaa<br>Pro Glu Leu Ser Val Ile Pro Gly Val Asn Ala Ala Ile Phe Glu Glu<br>945                    950                      955                      960 | 2880 |
| ctt gag gga cgt atc ttt acc gca ttc tcc ttg tac gat gcc aga aac<br>Leu Glu Gly Arg Ile Phe Thr Ala Phe Ser Leu Tyr Asp Ala Arg Asn<br>                965                      970                      975 | 2928 |
| gtc atc aag aac ggt gac ttc aac aat ggc ctc agc tgc tgg aat gtg<br>Val Ile Lys Asn Gly Asp Phe Asn Asn Gly Leu Ser Cys Trp Asn Val<br>         980                      985                      990 | 2976 |
| aaa ggt cat gtg gac gtg gag gaa   cag aac aat cag cgt   tcc gtc ctg<br>Lys Gly His Val Asp Val Glu Glu   Gln Asn Asn Gln Arg   Ser Val Leu<br>         995                      1000                  1005 | 3024 |
| gtt gtg   cct gag tgg gaa gct   gaa gtg tcc caa gag   gtt aga gtc<br>Val Val   Pro Glu Trp Glu Ala   Glu Val Ser Gln Glu   Val Arg Val<br>1010                        1015                      1020 | 3069 |
| tgt cca   ggt aga ggc tac att   ctc cgt gtg acc gct   tac aag gag<br>Cys Pro   Gly Arg Gly Tyr Ile   Leu Arg Val Thr Ala   Tyr Lys Glu<br>1025                        1030                      1035 | 3114 |
| gga tac   ggt gag ggt tgc gtg   acc atc cac gag atc   gag aac aac<br>Gly Tyr   Gly Glu Gly Cys Val   Thr Ile His Glu Ile   Glu Asn Asn<br>1040                        1045                      1050 | 3159 |
| acc gac   gag ctt aag ttc tcc   aac tgc gtc gag gaa   gaa atc tat<br>Thr Asp   Glu Leu Lys Phe Ser   Asn Cys Val Glu Glu   Glu Ile Tyr<br>1055                        1060                      1065 | 3204 |
| ccc aac   aac acc gtt act tgc   aac gac tac act gtg   aat cag gaa<br>Pro Asn   Asn Thr Val Thr Cys   Asn Asp Tyr Thr Val   Asn Gln Glu<br>1070                        1075                      1080 | 3249 |
| gag tac   gga ggt gcc tac act   agc cgt aac aga ggt   tac aac gaa<br>Glu Tyr   Gly Gly Ala Tyr Thr   Ser Arg Asn Arg Gly   Tyr Asn Glu<br>1085                        1090                      1095 | 3294 |
| gct cct   tcc gtt cct gct gac   tat gcc tcc gtg tac   gag gag aaa<br>Ala Pro   Ser Val Pro Ala Asp   Tyr Ala Ser Val Tyr   Glu Glu Lys<br>1100                        1105                      1110 | 3339 |
| tcc tac   aca gat ggc aga cgt   gag aac cct tgc gag   ttc aac aga<br>Ser Tyr   Thr Asp Gly Arg Arg   Glu Asn Pro Cys Glu   Phe Asn Arg<br>1115                        1120                      1125 | 3384 |
| ggt tac   agg gac tac aca cca   ctt cca gtt ggc tat   gtt acc aag<br>Gly Tyr   Arg Asp Tyr Thr Pro   Leu Pro Val Gly Tyr   Val Thr Lys<br>1130                        1135                      1140 | 3429 |
| gag ctt   gag tac ttt cct gag   acc gac aaa gtg tgg   atc gag atc<br>Glu Leu   Glu Tyr Phe Pro Glu   Thr Asp Lys Val Trp   Ile Glu Ile<br>1145                        1150                      1155 | 3474 |
| ggt gaa   acc gag gga acc ttc   atc gtg gac agc gtg   gag ctt ctc<br>Gly Glu   Thr Glu Gly Thr Phe   Ile Val Asp Ser Val   Glu Leu Leu<br>1160                        1165                      1170 | 3519 |
| ttg atg   gag gaa taa<br>Leu Met   Glu Glu<br>1175 | 3534 |

-continued

```
<210> SEQ ID NO 4
<211> LENGTH: 1177
<212> TYPE: PRT
<213> ORGANISM: artificial
<220> FEATURE:
<223> OTHER INFORMATION: Synthetic Construct

<400> SEQUENCE: 4
```

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp

-continued

```
            370                 375                 380
Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Arg Gln Gly Phe Ser His Arg Leu Ser His
            420                 425                 430

Val Ser Met Phe Arg Ser Gly Phe Ser Asn Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
                500                 505                 510

Val Asn Ile Asn Gly Gln Leu Pro Gln Arg Tyr Arg Ala Arg Ile Arg
            515                 520                 525

Tyr Ala Ser Thr Thr Asn Leu Arg Ile Tyr Val Thr Val Ala Gly Glu
530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
                580                 585                 590

Ser Gly Asn Glu Val Tyr Ile Asp Arg Phe Glu Leu Ile Pro Val Thr
            595                 600                 605

Ala Thr Leu Glu Ala Glu Tyr Asn Leu Glu Arg Ala Gln Lys Ala Val
            610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
                660                 665                 670

His Ala Lys Arg Leu Ser Asp Glu Arg Asn Leu Leu Gln Asp Ser Asn
            675                 680                 685

Phe Lys Asp Ile Asn Arg Gln Pro Glu Arg Gly Trp Gly Gly Ser Thr
690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Ser Ile Arg Tyr
            755                 760                 765

Asn Ala Lys His Glu Thr Val Asn Val Pro Gly Thr Gly Ser Leu Trp
            770                 775                 780

Pro Leu Ser Ala Gln Ser Pro Ile Gly Lys Cys Gly Glu Pro Asn Arg
785                 790                 795                 800
```

```
Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Lys Leu Glu Trp Glu
                885                 890                 895

Thr Asn Ile Val Tyr Lys Glu Ala Lys Glu Ser Val Asp Ala Leu Phe
                900                 905                 910

Val Asn Ser Gln Tyr Asp Gln Leu Gln Ala Asp Thr Asn Ile Ala Met
            915                 920                 925

Ile His Ala Ala Asp Lys Arg Val His Ser Ile Arg Glu Ala Tyr Leu
        930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
        995                 1000                1005

Val Val Pro Glu Trp Glu Ala Glu Val Ser Gln Glu Val Arg Val
    1010                1015                1020

Cys Pro Gly Arg Gly Tyr Ile Leu Arg Val Thr Ala Tyr Lys Glu
1025                1030                1035

Gly Tyr Gly Glu Gly Cys Val Thr Ile His Glu Ile Glu Asn Asn
    1040                1045                1050

Thr Asp Glu Leu Lys Phe Ser Asn Cys Val Glu Glu Glu Ile Tyr
    1055                1060                1065

Pro Asn Asn Thr Val Thr Cys Asn Asp Tyr Thr Val Asn Gln Glu
    1070                1075                1080

Glu Tyr Gly Gly Ala Tyr Thr Ser Arg Asn Arg Gly Tyr Asn Glu
    1085                1090                1095

Ala Pro Ser Val Pro Ala Asp Tyr Ala Ser Val Tyr Glu Glu Lys
    1100                1105                1110

Ser Tyr Thr Asp Gly Arg Arg Glu Asn Pro Cys Glu Phe Asn Arg
    1115                1120                1125

Gly Tyr Arg Asp Tyr Thr Pro Leu Pro Val Gly Tyr Val Thr Lys
    1130                1135                1140

Glu Leu Glu Tyr Phe Pro Glu Thr Asp Lys Val Trp Ile Glu Ile
    1145                1150                1155

Gly Glu Thr Glu Gly Thr Phe Ile Val Asp Ser Val Glu Leu Leu
    1160                1165                1170

Leu Met Glu Glu
    1175

<210> SEQ ID NO 5
<211> LENGTH: 5480
<212> TYPE: DNA
<213> ORGANISM: artificial
```

-continued

```
<220> FEATURE:
<223> OTHER INFORMATION: expression cassette encoding Cry1A.105 amino
      acid sequence
<220> FEATURE:
<221> NAME/KEY: promoter
<222> LOCATION: (1)..(981)
<223> OTHER INFORMATION: FMV.e35S promoter
<220> FEATURE:
<221> NAME/KEY: 5'UTR
<222> LOCATION: (985)..(1080)
<220> FEATURE:
<221> NAME/KEY: transit_peptide
<222> LOCATION: (1090)..(1263)
<223> OTHER INFORMATION: chloroplast targeting peptide sequence
<220> FEATURE:
<221> NAME/KEY: CDS
<222> LOCATION: (1267)..(4797)
<223> OTHER INFORMATION: coding sequence for Cry1A.105
<220> FEATURE:
<221> NAME/KEY: terminator
<222> LOCATION: (4833)..(5480)
<223> OTHER INFORMATION: Ps.E9 rbcS transcription termination and
      polyadenylation sequence

<400> SEQUENCE: 5
aattctcagt ccaaagcctc aacaaggtca gggtacagag tctccaaacc attagccaaa      60
agctacagga gatcaatgaa gaatcttcaa tcaaagtaaa ctactgttcc agcacatgca     120
tcatggtcag taagtttcag aaaaagacat ccaccgaaga cttaaagtta gtgggcatct     180
ttgaaagtaa tcttgtcaac atcgagcagc tggcttgtgg ggaccagaca aaaaaggaat     240
ggtgcagaat tgttaggcgc acctaccaaa agcatctttg cctttattgc aaagataaag     300
cagattcctc tagtacaagt ggggaacaaa ataacgtgga aaagagctgt cctgacagcc     360
cactcactaa tgcgtatgac gaacgcagtg acgaccacaa agaattagc ttgagctcag     420 gatttagcag cattccagat tgggttcaat caacaaggta cgagccatat cactttattc     480
aaattggtat cgccaaaacc aagaaggaac tcccatcctc aaaggtttgt aaggaagaat     540
tctcagtcca aagcctcaac aaggtcaggg tacagagtct ccaaaccatt agccaaaagc     600
tacaggagat caatgaagaa tcttcaatca agtaaacta ctgttccagc acatgcatca     660
tggtcagtaa gtttcagaaa aagacatcca ccgaagactt aaagttagtg gcatctttg     720 aaagtaatct tgtcaacatc gagcagctgg cttgtgggga ccagacaaaa aaggaatggt     780
gcagaattgt taggcgcacc taccaaaagc atctttgcct ttattgcaaa gataaagcag     840
attcctctag tacaagtggg gaacaaaata cgtggaaaa gagctgtcct gacagcccac     900
tcactaatgc gtatgacgaa cgcagtgacg accacaaaag aattccctct atataagaag     960
gcattcattc ccatttgaag gacacagaaa aatttgctac attgtttcac aaacttcaaa    1020
tattattcat ttatttgtca gctttcaaac tctttgtttc ttgtttgttg attgagaata    1080
tttaaaacaa tggcttcctc tatgctctct tccgctacta tggttgcctc tccggctcag    1140
gccactatgg tcgctccttt caacggactt aagtcctccg ctgccttccc agccaccgc     1200 aaggctaaca acgacattac ttccatcaca agcaacggcg gaagagttaa ctgcatgcag    1260 gccatg gac aac aac cca aac atc aac gaa tgc att cca tac aac tgc        1308
       Asp Asn Asn Pro Asn Ile Asn Glu Cys Ile Pro Tyr Asn Cys
       1               5                   10 ttg agt aac cca gaa gtt gaa gta ctt ggt gga gaa cgc att gaa acc       1356
Leu Ser Asn Pro Glu Val Glu Val Leu Gly Gly Glu Arg Ile Glu Thr
15                  20                  25                  30 ggt tac act ccc atc gac atc tcc ttg tcc ttg aca cag ttt ctg ctc       1404
Gly Tyr Thr Pro Ile Asp Ile Ser Leu Ser Leu Thr Gln Phe Leu Leu
                35                  40                  45
```

|  |  |  |  |  |  |  |  |  |  |  |  |  |  |  |  |
|---|---|---|---|---|---|---|---|---|---|---|---|---|---|---|---|
| agc | gag | ttc | gtg | cca | ggt | gct | ggg | ttc | gtt | ctc | gga | cta | gtt | gac | atc | 1452 |
| Ser | Glu | Phe | Val | Pro | Gly | Ala | Gly | Phe | Val | Leu | Gly | Leu | Val | Asp | Ile |
|  |  |  | 50 |  |  |  | 55 |  |  |  |  | 60 |  |  |  |

| atc | tgg | ggt | atc | ttt | ggt | cca | tct | caa | tgg | gat | gca | ttc | ctg | gtg | caa | 1500 |
| Ile | Trp | Gly | Ile | Phe | Gly | Pro | Ser | Gln | Trp | Asp | Ala | Phe | Leu | Val | Gln |
|  |  | 65 |  |  |  |  | 70 |  |  |  |  | 75 |  |  |  |

| att | gag | cag | ttg | atc | aac | cag | agg | atc | gaa | gag | ttc | gcc | agg | aac | cag | 1548 |
| Ile | Glu | Gln | Leu | Ile | Asn | Gln | Arg | Ile | Glu | Glu | Phe | Ala | Arg | Asn | Gln |
| 80 |  |  |  |  | 85 |  |  |  |  | 90 |  |  |  |  |  |

| gcc | atc | tct | agg | ttg | gaa | gga | ttg | agc | aat | ctc | tac | caa | atc | tat | gca | 1596 |
| Ala | Ile | Ser | Arg | Leu | Glu | Gly | Leu | Ser | Asn | Leu | Tyr | Gln | Ile | Tyr | Ala |
| 95 |  |  |  |  | 100 |  |  |  |  | 105 |  |  |  |  | 110 |

| gag | agc | ttc | aga | gag | tgg | gaa | gcc | gat | cct | act | aac | cca | gct | ctc | cgc | 1644 |
| Glu | Ser | Phe | Arg | Glu | Trp | Glu | Ala | Asp | Pro | Thr | Asn | Pro | Ala | Leu | Arg |
|  |  |  |  | 115 |  |  |  |  | 120 |  |  |  |  | 125 |  |

| gag | gaa | atg | cgt | att | caa | ttc | aac | gac | atg | aac | agc | gcc | ttg | acc | aca | 1692 |
| Glu | Glu | Met | Arg | Ile | Gln | Phe | Asn | Asp | Met | Asn | Ser | Ala | Leu | Thr | Thr |
|  |  |  | 130 |  |  |  |  | 135 |  |  |  |  | 140 |  |  |

| gct | atc | cca | ttg | ttc | gca | gtc | cag | aac | tac | caa | gtt | cct | ctc | ttg | tcc | 1740 |
| Ala | Ile | Pro | Leu | Phe | Ala | Val | Gln | Asn | Tyr | Gln | Val | Pro | Leu | Leu | Ser |
|  |  | 145 |  |  |  |  | 150 |  |  |  |  | 155 |  |  |  |

| gtg | tac | gtt | caa | gca | gct | aat | ctt | cac | ctc | agc | gtg | ctt | cga | gac | gtt | 1788 |
| Val | Tyr | Val | Gln | Ala | Ala | Asn | Leu | His | Leu | Ser | Val | Leu | Arg | Asp | Val |
|  | 160 |  |  |  |  | 165 |  |  |  |  | 170 |  |  |  |  |

| agc | gtg | ttt | ggg | caa | agg | tgg | gga | ttc | gat | gct | gca | acc | atc | aat | agc | 1836 |
| Ser | Val | Phe | Gly | Gln | Arg | Trp | Gly | Phe | Asp | Ala | Ala | Thr | Ile | Asn | Ser |
| 175 |  |  |  |  | 180 |  |  |  |  | 185 |  |  |  |  | 190 |

| cgt | tac | aac | gac | ctt | act | agg | ctg | att | gga | aac | tac | acc | gac | cac | gct | 1884 |
| Arg | Tyr | Asn | Asp | Leu | Thr | Arg | Leu | Ile | Gly | Asn | Tyr | Thr | Asp | His | Ala |
|  |  |  |  | 195 |  |  |  |  | 200 |  |  |  |  | 205 |  |

| gtt | cgt | tgg | tac | aac | act | ggc | ttg | gag | cgt | gtc | tgg | ggt | cct | gat | tct | 1932 |
| Val | Arg | Trp | Tyr | Asn | Thr | Gly | Leu | Glu | Arg | Val | Trp | Gly | Pro | Asp | Ser |
|  |  |  | 210 |  |  |  |  | 215 |  |  |  |  | 220 |  |  |

| aga | gat | tgg | att | aga | tac | aac | cag | ttc | agg | aga | gaa | ttg | acc | ctc | aca | 1980 |
| Arg | Asp | Trp | Ile | Arg | Tyr | Asn | Gln | Phe | Arg | Arg | Glu | Leu | Thr | Leu | Thr |
|  |  | 225 |  |  |  |  | 230 |  |  |  |  | 235 |  |  |  |

| gtt | ttg | gac | att | gtg | tct | ctc | ttc | ccg | aac | tat | gac | tcc | aga | acc | tac | 2028 |
| Val | Leu | Asp | Ile | Val | Ser | Leu | Phe | Pro | Asn | Tyr | Asp | Ser | Arg | Thr | Tyr |
|  | 240 |  |  |  |  | 245 |  |  |  |  | 250 |  |  |  |  |

| cct | atc | cgt | aca | gtg | tcc | caa | ctt | acc | aga | gaa | atc | tat | act | aac | cca | 2076 |
| Pro | Ile | Arg | Thr | Val | Ser | Gln | Leu | Thr | Arg | Glu | Ile | Tyr | Thr | Asn | Pro |
| 255 |  |  |  |  | 260 |  |  |  |  | 265 |  |  |  |  | 270 |

| gtt | ctt | gag | aac | ttc | gac | ggt | agc | ttc | cgt | ggt | tct | gcc | caa | ggt | atc | 2124 |
| Val | Leu | Glu | Asn | Phe | Asp | Gly | Ser | Phe | Arg | Gly | Ser | Ala | Gln | Gly | Ile |
|  |  |  |  | 275 |  |  |  |  | 280 |  |  |  |  | 285 |  |

| gaa | ggc | tcc | atc | agg | agc | cca | cac | ttg | atg | gac | atc | ttg | aac | agc | ata | 2172 |
| Glu | Gly | Ser | Ile | Arg | Ser | Pro | His | Leu | Met | Asp | Ile | Leu | Asn | Ser | Ile |
|  |  |  | 290 |  |  |  |  | 295 |  |  |  |  | 300 |  |  |

| act | atc | tac | acc | gat | gct | cac | aga | gga | gag | tat | tac | tgg | tct | gga | cac | 2220 |
| Thr | Ile | Tyr | Thr | Asp | Ala | His | Arg | Gly | Glu | Tyr | Tyr | Trp | Ser | Gly | His |
|  |  | 305 |  |  |  |  | 310 |  |  |  |  | 315 |  |  |  |

| cag | atc | atg | gcc | tct | cca | gtt | gga | ttc | agc | ggg | ccc | gag | ttt | acc | ttt | 2268 |
| Gln | Ile | Met | Ala | Ser | Pro | Val | Gly | Phe | Ser | Gly | Pro | Glu | Phe | Thr | Phe |
|  | 320 |  |  |  |  | 325 |  |  |  |  | 330 |  |  |  |  |

| cct | ctc | tat | gga | act | atg | gga | aac | gcc | gct | cca | caa | caa | cgt | atc | gtt | 2316 |
| Pro | Leu | Tyr | Gly | Thr | Met | Gly | Asn | Ala | Ala | Pro | Gln | Gln | Arg | Ile | Val |
| 335 |  |  |  |  | 340 |  |  |  |  | 345 |  |  |  |  | 350 |

| gct | caa | cta | ggt | cag | ggt | gtc | tac | aga | acc | ttg | tct | tcc | acc | ttg | tac | 2364 |
| Ala | Gln | Leu | Gly | Gln | Gly | Val | Tyr | Arg | Thr | Leu | Ser | Ser | Thr | Leu | Tyr |
|  |  |  |  | 355 |  |  |  |  | 360 |  |  |  |  | 365 |  |

| | | |
|---|---|---|
| aga aga ccc ttc aat atc ggt atc aac aac cag caa ctt tcc gtt ctt<br>Arg Arg Pro Phe Asn Ile Gly Ile Asn Asn Gln Gln Leu Ser Val Leu<br>370                       375                      380 | | 2412 |
| gac gga aca gag ttc gcc tat gga acc tct tct aac ttg cca tcc gct<br>Asp Gly Thr Glu Phe Ala Tyr Gly Thr Ser Ser Asn Leu Pro Ser Ala<br>            385                       390                      395 | | 2460 |
| gtt tac aga aag agc gga acc gtt gat tcc ttg gac gaa atc cca cca<br>Val Tyr Arg Lys Ser Gly Thr Val Asp Ser Leu Asp Glu Ile Pro Pro<br>400                       405                       410 | | 2508 |
| cag aac aac aat gtg cca ccc agg caa gga ttc tcc cac agg ttg agc<br>Gln Asn Asn Asn Val Pro Pro Arg Gln Gly Phe Ser His Arg Leu Ser<br>415                       420                      425               430 | | 2556 |
| cac gtg tcc atg ttc cgt tcc gga ttc agc aac agt tcc gtg agc atc<br>His Val Ser Met Phe Arg Ser Gly Phe Ser Asn Ser Ser Val Ser Ile<br>                     435                       440                      445 | | 2604 |
| atc aga gct cct atg ttc tct tgg ata cac cgt agt gct gag ttc aac<br>Ile Arg Ala Pro Met Phe Ser Trp Ile His Arg Ser Ala Glu Phe Asn<br>                     450                       455                      460 | | 2652 |
| aac atc att gca tcc gac agc att act caa ata ccc ttg gtg aaa gca<br>Asn Ile Ile Ala Ser Asp Ser Ile Thr Gln Ile Pro Leu Val Lys Ala<br>465                       470                       475 | | 2700 |
| cat aca ctt cag tca ggt act act gtt gtc aga ggt cca ggg ttt aca<br>His Thr Leu Gln Ser Gly Thr Thr Val Val Arg Gly Pro Gly Phe Thr<br>480                       485                      490 | | 2748 |
| gga gga gac att ctt cgt cgc aca agt gga gga ccc ttt gct tac act<br>Gly Gly Asp Ile Leu Arg Arg Thr Ser Gly Gly Pro Phe Ala Tyr Thr<br>495                       500                      505               510 | | 2796 |
| att gtt aac atc aat ggc caa ttg ccc caa agg tat cgt gca aga atc<br>Ile Val Asn Ile Asn Gly Gln Leu Pro Gln Arg Tyr Arg Ala Arg Ile<br>                     515                       520                      525 | | 2844 |
| cgc tat gcc tct act aca aat ctc agg atc tac gtg act gtt gca ggt<br>Arg Tyr Ala Ser Thr Thr Asn Leu Arg Ile Tyr Val Thr Val Ala Gly<br>530                       535                      540 | | 2892 |
| gaa agg atc ttt gct ggt cag ttc aac aag act atg gat acc ggt gac<br>Glu Arg Ile Phe Ala Gly Gln Phe Asn Lys Thr Met Asp Thr Gly Asp<br>                   545                       550                      555 | | 2940 |
| cct ttg aca ttc caa tct ttt agc tac gca act atc aac aca gct ttt<br>Pro Leu Thr Phe Gln Ser Phe Ser Tyr Ala Thr Ile Asn Thr Ala Phe<br>560                       565                       570 | | 2988 |
| aca ttc cca atg agc cag agt agc ttc aca gta ggt gct gac act ttc<br>Thr Phe Pro Met Ser Gln Ser Ser Phe Thr Val Gly Ala Asp Thr Phe<br>575                       580                      585               590 | | 3036 |
| agc tca ggg aat gaa gtt tac atc gac agg ttt gaa ttg att cca gtt<br>Ser Ser Gly Asn Glu Val Tyr Ile Asp Arg Phe Glu Leu Ile Pro Val<br>                     595                       600                     605 | | 3084 |
| act gca acc ctc gag gct gag tac aac ctt gag aga gcc cag aag gct<br>Thr Ala Thr Leu Glu Ala Glu Tyr Asn Leu Glu Arg Ala Gln Lys Ala<br>                     610                       615                     620 | | 3132 |
| gtg aac gcc ctc ttt acc tcc acc aat cag ctt ggc ttg aaa act aac<br>Val Asn Ala Leu Phe Thr Ser Thr Asn Gln Leu Gly Leu Lys Thr Asn<br>625                       630                      635 | | 3180 |
| gtt act gac tat cac att gac caa gtg tcc aac ttg gtc acc tac ctt<br>Val Thr Asp Tyr His Ile Asp Gln Val Ser Asn Leu Val Thr Tyr Leu<br>640                       645                       650 | | 3228 |
| agc gat gag ttc tgc ctc gac gag aag cgt gaa ctc tcc gag aaa gtt<br>Ser Asp Glu Phe Cys Leu Asp Glu Lys Arg Glu Leu Ser Glu Lys Val<br>655                       660                       665                     670 | | 3276 |
| aaa cac gcc aag cgt ctc agc gac gag agg aat ctc ttg caa gac tcc<br>Lys His Ala Lys Arg Leu Ser Asp Glu Arg Asn Leu Leu Gln Asp Ser<br>                     675                       680                     685 | | 3324 |

```
aac ttc aaa gac atc aac agg cag cca gaa cgt ggt tgg ggt gga agc      3372
Asn Phe Lys Asp Ile Asn Arg Gln Pro Glu Arg Gly Trp Gly Gly Ser
            690                 695                 700 acc ggg atc acc atc caa gga ggc gac gat gtg ttc aag gag aac tac      3420
Thr Gly Ile Thr Ile Gln Gly Gly Asp Asp Val Phe Lys Glu Asn Tyr
        705                 710                 715 gtc acc ctc tcc gga act ttc gac gag tgc tac cct acc tac ttg tac      3468
Val Thr Leu Ser Gly Thr Phe Asp Glu Cys Tyr Pro Thr Tyr Leu Tyr
    720                 725                 730 cag aag atc gat gag tcc aaa ctc aaa gcc ttc acc agg tat caa ctt      3516
Gln Lys Ile Asp Glu Ser Lys Leu Lys Ala Phe Thr Arg Tyr Gln Leu
735                 740                 745                 750 aga ggc tac atc gaa gac agc caa gac ctt gaa atc tac tcg atc agg      3564
Arg Gly Tyr Ile Glu Asp Ser Gln Asp Leu Glu Ile Tyr Ser Ile Arg
                755                 760                 765 tac aat gcc aag cac gag acc gtg aat gtc cca ggt act ggt tcc ctc      3612
Tyr Asn Ala Lys His Glu Thr Val Asn Val Pro Gly Thr Gly Ser Leu
            770                 775                 780 tgg cca ctt tct gcc caa tct ccc att ggg aag tgt gga gag cct aac      3660
Trp Pro Leu Ser Ala Gln Ser Pro Ile Gly Lys Cys Gly Glu Pro Asn
        785                 790                 795 aga tgc gct cca cac ctt gag tgg aat cct gac ttg gac tgc tcc tgc      3708
Arg Cys Ala Pro His Leu Glu Trp Asn Pro Asp Leu Asp Cys Ser Cys
    800                 805                 810 agg gat ggc gag aag tgt gcc cac cat tct cat cac ttc tcc ttg gac      3756
Arg Asp Gly Glu Lys Cys Ala His His Ser His His Phe Ser Leu Asp
815                 820                 825                 830 atc gat gtg gga tgt act gac ctg aat gag gac ctc gga gtc tgg gtc      3804
Ile Asp Val Gly Cys Thr Asp Leu Asn Glu Asp Leu Gly Val Trp Val
                835                 840                 845 atc ttc aag atc aag acc caa gac gga cac gca aga ctt ggc aac ctt      3852
Ile Phe Lys Ile Lys Thr Gln Asp Gly His Ala Arg Leu Gly Asn Leu
            850                 855                 860 gag ttt ctc gaa gag aaa cca ttg gtc ggt gaa gct ctc gct cgt gtg      3900
Glu Phe Leu Glu Glu Lys Pro Leu Val Gly Glu Ala Leu Ala Arg Val
        865                 870                 875 aag aga gca gag aag aag tgg agg gac aaa cgt gag aaa ctc gaa tgg      3948
Lys Arg Ala Glu Lys Lys Trp Arg Asp Lys Arg Glu Lys Leu Glu Trp
    880                 885                 890 gaa act aac atc gtt tac aag gag gcc aaa gag tcc gtg gat gct ttg      3996
Glu Thr Asn Ile Val Tyr Lys Glu Ala Lys Glu Ser Val Asp Ala Leu
895                 900                 905                 910 ttc gtg aac tcc caa tat gat cag ttg caa gcc gac acc aac atc gcc      4044
Phe Val Asn Ser Gln Tyr Asp Gln Leu Gln Ala Asp Thr Asn Ile Ala
                915                 920                 925 atg atc cac gcc gca gac aaa cgt gtg cac agc att cgt gag gct tac      4092
Met Ile His Ala Ala Asp Lys Arg Val His Ser Ile Arg Glu Ala Tyr
            930                 935                 940 ttg cct gag ttg tcc gtg atc cct ggt gtg aac gct gcc atc ttc gag      4140
Leu Pro Glu Leu Ser Val Ile Pro Gly Val Asn Ala Ala Ile Phe Glu
        945                 950                 955 gaa ctt gag gga cgt atc ttt acc gca ttc tcc ttg tac gat gcc aga      4188
Glu Leu Glu Gly Arg Ile Phe Thr Ala Phe Ser Leu Tyr Asp Ala Arg
    960                 965                 970 aac gtc atc aag aac ggt gac ttc aac aat ggc ctc agc tgc tgg aat      4236
Asn Val Ile Lys Asn Gly Asp Phe Asn Asn Gly Leu Ser Cys Trp Asn
975                 980                 985                 990 gtg aaa ggt cat gtg gac gtg gag gaa cag  aac aat cag cgt tcc  gtc    4284
Val Lys Gly His Val Asp Val Glu Glu Gln Asn Asn Gln Arg Ser  Val
                995                 1000                1005
```

-continued

| | | | | | | | | | | | |
|---|---|---|---|---|---|---|---|---|---|---|---|
| ctg | gtt | gtg | cct | gag | tgg | gaa | gct | gaa | gtg | tcc | caa gag gtt aga | 4329 |
| Leu | Val | Val | Pro | Glu | Trp | Glu | Ala | Glu | Val | Ser | Gln Glu Val Arg |
| | | | 1010 | | | | 1015 | | | | 1020 |

```
ctg gtt gtg cct gag tgg gaa gct gaa gtg tcc caa gag gtt aga          4329
Leu Val Val Pro Glu Trp Glu Ala Glu Val Ser Gln Glu Val Arg
            1010                1015                1020 gtc tgt cca ggt aga ggc tac att ctc cgt gtg acc gct tac aag          4374
Val Cys Pro Gly Arg Gly Tyr Ile Leu Arg Val Thr Ala Tyr Lys
            1025                1030                1035 gag gga tac ggt gag ggt tgc gtg acc atc cac gag atc gag aac          4419
Glu Gly Tyr Gly Glu Gly Cys Val Thr Ile His Glu Ile Glu Asn
            1040                1045                1050 aac acc gac gag ctt aag ttc tcc aac tgc gtc gag gaa gaa atc          4464
Asn Thr Asp Glu Leu Lys Phe Ser Asn Cys Val Glu Glu Glu Ile
            1055                1060                1065 tat ccc aac aac acc gtt act tgc aac gac tac act gtg aat cag          4509
Tyr Pro Asn Asn Thr Val Thr Cys Asn Asp Tyr Thr Val Asn Gln
            1070                1075                1080 gaa gag tac gga ggt gcc tac act agc cgt aac aga ggt tac aac          4554
Glu Glu Tyr Gly Gly Ala Tyr Thr Ser Arg Asn Arg Gly Tyr Asn
            1085                1090                1095 gaa gct cct tcc gtt cct gct gac tat gcc tcc gtg tac gag gag          4599
Glu Ala Pro Ser Val Pro Ala Asp Tyr Ala Ser Val Tyr Glu Glu
            1100                1105                1110 aaa tcc tac aca gat ggc aga cgt gag aac cct tgc gag ttc aac          4644
Lys Ser Tyr Thr Asp Gly Arg Arg Glu Asn Pro Cys Glu Phe Asn
            1115                1120                1125 aga ggt tac agg gac tac aca cca ctt cca gtt ggc tat gtt acc          4689
Arg Gly Tyr Arg Asp Tyr Thr Pro Leu Pro Val Gly Tyr Val Thr
            1130                1135                1140 aag gag ctt gag tac ttt cct gag acc gac aaa gtg tgg atc gag          4734
Lys Glu Leu Glu Tyr Phe Pro Glu Thr Asp Lys Val Trp Ile Glu
            1145                1150                1155 atc ggt gaa acc gag gga acc ttc atc gtg gac agc gtg gag ctt          4779
Ile Gly Glu Thr Glu Gly Thr Phe Ile Val Asp Ser Val Glu Leu
            1160                1165                1170 ctc ttg atg gag gaa taa tgagatccac gatatcctgc aggaattggc             4827
Leu Leu Met Glu Glu
            1175 cggccagctt tcgttcgtat catcggtttc gacaacgttc gtcaagttca atgcatcagt    4887 ttcattgcgc acacaccaga atcctactga gtttgagtat tatggcattg ggaaaactgt    4947 ttttcttgta ccatttgttg tgcttgtaat ttactgtgtt ttttattcgg ttttcgctat    5007 cgaactgtga atggaaatg gatggagaag agttaatgaa tgatatggtc cttttgttca     5067 ttctcaaatt aatattattt gttttttctc ttatttgttg tgtgttgaat ttgaaattat    5127 aagagatatg caaacatttt gttttgagta aaaatgtgtc aaatcgtggc ctctaatgac    5187 cgaagttaat atgaggagta aaacacttgt agttgtacca ttatgcttat tcactaggca    5247 acaaatatat tttcagacct agaaaagctg caaatgttac tgaatacaag tatgtcctct    5307 tgtgttttag acatttatgg actttccttt atgtaatttt ccagaatcct tgtcagattc    5367 taatcattgc tttataatta tagttatact catggatttg tagttgagta tgaaaatatt    5427 ttttaatgca ttttatgact tgccaattga ttgacaacat gcatcaatcg acc           5480
```

<210> SEQ ID NO 6
<211> LENGTH: 1176
<212> TYPE: PRT
<213> ORGANISM: artificial
<220> FEATURE:
<223> OTHER INFORMATION: Synthetic Construct

<400> SEQUENCE: 6

```
Asp Asn Asn Pro Asn Ile Asn Glu Cys Ile Pro Tyr Asn Cys Leu Ser
1               5                   10                  15

Asn Pro Glu Val Glu Val Leu Gly Gly Glu Arg Ile Glu Thr Gly Tyr
            20                  25                  30

Thr Pro Ile Asp Ile Ser Leu Ser Leu Thr Gln Phe Leu Leu Ser Glu
            35                  40                  45

Phe Val Pro Gly Ala Gly Phe Val Gly Leu Val Asp Ile Ile Trp
50                  55                  60

Gly Ile Phe Gly Pro Ser Gln Trp Asp Ala Phe Leu Val Gln Ile Glu
65                  70                  75                  80

Gln Leu Ile Asn Gln Arg Ile Glu Glu Phe Ala Arg Asn Gln Ala Ile
                85                  90                  95

Ser Arg Leu Glu Gly Leu Ser Asn Leu Tyr Gln Ile Tyr Ala Glu Ser
                100                 105                 110

Phe Arg Glu Trp Glu Ala Asp Pro Thr Asn Pro Ala Leu Arg Glu Glu
                115                 120                 125

Met Arg Ile Gln Phe Asn Asp Met Asn Ser Ala Leu Thr Thr Ala Ile
    130                 135                 140

Pro Leu Phe Ala Val Gln Asn Tyr Gln Val Pro Leu Leu Ser Val Tyr
145                 150                 155                 160

Val Gln Ala Ala Asn Leu His Leu Ser Val Leu Arg Asp Val Ser Val
                165                 170                 175

Phe Gly Gln Arg Trp Gly Phe Asp Ala Ala Thr Ile Asn Ser Arg Tyr
                180                 185                 190

Asn Asp Leu Thr Arg Leu Ile Gly Asn Tyr Thr Asp His Ala Val Arg
                195                 200                 205

Trp Tyr Asn Thr Gly Leu Glu Arg Val Trp Gly Pro Asp Ser Arg Asp
210                 215                 220

Trp Ile Arg Tyr Asn Gln Phe Arg Arg Glu Leu Thr Leu Thr Val Leu
225                 230                 235                 240

Asp Ile Val Ser Leu Phe Pro Asn Tyr Asp Ser Arg Thr Tyr Pro Ile
                245                 250                 255

Arg Thr Val Ser Gln Leu Thr Arg Glu Ile Tyr Thr Asn Pro Val Leu
                260                 265                 270

Glu Asn Phe Asp Gly Ser Phe Arg Gly Ser Ala Gln Gly Ile Glu Gly
                275                 280                 285

Ser Ile Arg Ser Pro His Leu Met Asp Ile Leu Asn Ser Ile Thr Ile
    290                 295                 300

Tyr Thr Asp Ala His Arg Gly Glu Tyr Tyr Trp Ser Gly His Gln Ile
305                 310                 315                 320

Met Ala Ser Pro Val Gly Phe Ser Gly Pro Glu Phe Thr Phe Pro Leu
                325                 330                 335

Tyr Gly Thr Met Gly Asn Ala Ala Pro Gln Gln Arg Ile Val Ala Gln
            340                 345                 350

Leu Gly Gln Gly Val Tyr Arg Thr Leu Ser Ser Thr Leu Tyr Arg Arg
        355                 360                 365

Pro Phe Asn Ile Gly Ile Asn Asn Gln Gln Leu Ser Val Leu Asp Gly
    370                 375                 380

Thr Glu Phe Ala Tyr Gly Thr Ser Ser Asn Leu Pro Ser Ala Val Tyr
385                 390                 395                 400

Arg Lys Ser Gly Thr Val Asp Ser Leu Asp Glu Ile Pro Pro Gln Asn
            405                 410                 415

Asn Asn Val Pro Pro Arg Gln Gly Phe Ser His Arg Leu Ser His Val
            420                 425                 430
```

Ser Met Phe Arg Ser Gly Phe Ser Asn Ser Val Ser Ile Ile Arg
        435                 440                 445

Ala Pro Met Phe Ser Trp Ile His Arg Ser Ala Glu Phe Asn Asn Ile
450                 455                 460

Ile Ala Ser Asp Ser Ile Thr Gln Ile Pro Leu Val Lys Ala His Thr
465                 470                 475                 480

Leu Gln Ser Gly Thr Thr Val Val Arg Gly Pro Gly Phe Thr Gly Gly
                    485                 490                 495

Asp Ile Leu Arg Arg Thr Ser Gly Gly Pro Phe Ala Tyr Thr Ile Val
                500                 505                 510

Asn Ile Asn Gly Gln Leu Pro Gln Arg Tyr Arg Ala Arg Ile Arg Tyr
            515                 520                 525

Ala Ser Thr Thr Asn Leu Arg Ile Tyr Val Thr Val Ala Gly Glu Arg
        530                 535                 540

Ile Phe Ala Gly Gln Phe Asn Lys Thr Met Asp Thr Gly Asp Pro Leu
545                 550                 555                 560

Thr Phe Gln Ser Phe Ser Tyr Ala Thr Ile Asn Thr Ala Phe Thr Phe
                    565                 570                 575

Pro Met Ser Gln Ser Ser Phe Thr Val Gly Ala Asp Thr Phe Ser Ser
                580                 585                 590

Gly Asn Glu Val Tyr Ile Asp Arg Phe Glu Leu Ile Pro Val Thr Ala
            595                 600                 605

Thr Leu Glu Ala Glu Tyr Asn Leu Glu Arg Ala Gln Lys Ala Val Asn
        610                 615                 620

Ala Leu Phe Thr Ser Thr Asn Gln Leu Gly Leu Lys Thr Asn Val Thr
625                 630                 635                 640

Asp Tyr His Ile Asp Gln Val Ser Asn Leu Val Thr Tyr Leu Ser Asp
                    645                 650                 655

Glu Phe Cys Leu Asp Glu Lys Arg Glu Leu Ser Glu Lys Val Lys His
                660                 665                 670

Ala Lys Arg Leu Ser Asp Glu Arg Asn Leu Leu Gln Asp Ser Asn Phe
            675                 680                 685

Lys Asp Ile Asn Arg Gln Pro Glu Arg Gly Trp Gly Gly Ser Thr Gly
        690                 695                 700

Ile Thr Ile Gln Gly Gly Asp Asp Val Phe Lys Glu Asn Tyr Val Thr
705                 710                 715                 720

Leu Ser Gly Thr Phe Asp Glu Cys Tyr Pro Thr Tyr Leu Tyr Gln Lys
                    725                 730                 735

Ile Asp Glu Ser Lys Leu Lys Ala Phe Thr Arg Tyr Gln Leu Arg Gly
                740                 745                 750

Tyr Ile Glu Asp Ser Gln Asp Leu Glu Ile Tyr Ser Ile Arg Tyr Asn
            755                 760                 765

Ala Lys His Glu Thr Val Asn Val Pro Gly Thr Gly Ser Leu Trp Pro
        770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                    805                 810                 815

Gly Glu Lys Cys Ala His His Ser His His Phe Ser Leu Asp Ile Asp
                820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe

```
    850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln  Asn Asn Gln Arg Ser  Val Leu Val
        995                 1000                1005

Val Pro  Glu Trp Glu Ala Glu  Val Ser Gln Glu Val  Arg Val Cys
    1010                 1015                 1020

Pro Gly  Arg Gly Tyr Ile Leu  Arg Val Thr Ala Tyr  Lys Glu Gly
    1025                 1030                 1035

Tyr Gly  Glu Gly Cys Val Thr  Ile His Glu Ile Glu  Asn Asn Thr
    1040                 1045                 1050

Asp Glu  Leu Lys Phe Ser Asn  Cys Val Glu Glu Glu  Ile Tyr Pro
    1055                 1060                 1065

Asn Asn  Thr Val Thr Cys Asn  Asp Tyr Thr Val Asn  Gln Glu Glu
    1070                 1075                 1080

Tyr Gly  Gly Ala Tyr Thr Ser  Arg Asn Arg Gly Tyr  Asn Glu Ala
    1085                 1090                 1095

Pro Ser  Val Pro Ala Asp Tyr  Ala Ser Val Tyr Glu  Glu Lys Ser
    1100                 1105                 1110

Tyr Thr  Asp Gly Arg Arg Glu  Asn Pro Cys Glu Phe  Asn Arg Gly
    1115                 1120                 1125

Tyr Arg  Asp Tyr Thr Pro Leu  Pro Val Gly Tyr Val  Thr Lys Glu
    1130                 1135                 1140

Leu Glu  Tyr Phe Pro Glu Thr  Asp Lys Val Trp Ile  Glu Ile Gly
    1145                 1150                 1155

Glu Thr  Glu Gly Thr Phe Ile  Val Asp Ser Val Glu  Leu Leu Leu
    1160                 1165                 1170

Met Glu  Glu
    1175

<210> SEQ ID NO 7
<211> LENGTH: 4990
<212> TYPE: DNA
<213> ORGANISM: artificial
<220> FEATURE:
<223> OTHER INFORMATION: expression cassette encoding Cry1A.105 amino
      acid sequence
<220> FEATURE:
<221> NAME/KEY: promoter
<222> LOCATION: (1)..(614)
<223> OTHER INFORMATION: CAMV e35s promoter
<220> FEATURE:
<221> NAME/KEY: 5'UTR
<222> LOCATION: (650)..(710)
```

```
<220> FEATURE:
<221> NAME/KEY: Intron
<222> LOCATION: (727)..(1206)
<223> OTHER INFORMATION: rice actin intron RACT1
<220> FEATURE:
<221> NAME/KEY: CDS
<222> LOCATION: (1216)..(4752)
<223> OTHER INFORMATION: coding sequence for Cry1A.105
<220> FEATURE:
<221> NAME/KEY: terminator
<222> LOCATION: (4781)..(4990)
<223> OTHER INFORMATION: Ta.Hsp17 transcription termination and
     polyadenylation sequence

<400> SEQUENCE: 7
```

| | | | | | |
|---|---|---|---|---|---|
| ggtccgatgt | gagactttc | aacaaagggt | aatatccgga | aacctcctcg | gattccattg | 60 |
| cccagctatc | tgtcactta | ttgtgaagat | agtggaaaag | gaaggtggct | cctacaaatg | 120 |
| ccatcattgc | gataaaggaa | aggccatcgt | tgaagatgcc | tctgccgaca | gtggtcccaa | 180 |
| agatggaccc | ccacccacga | ggagcatcgt | ggaaaaagaa | gacgttccaa | ccacgtcttc | 240 |
| aaagcaagtg | gattgatgtg | atggtccgat | gtgagacttt | tcaacaaagg | gtaatatccg | 300 |
| gaaacctcct | cggattccat | tgcccagcta | tctgtcactt | tattgtgaag | atagtggaaa | 360 |
| aggaaggtgg | ctcctacaaa | tgccatcatt | gcgataaagg | aaaggccatc | gttgaagatg | 420 |
| cctctgccga | cagtggtccc | aaagatggac | ccccacccac | gaggagcatc | gtggaaaaag | 480 |
| aagacgttcc | aaccacgtct | tcaaagcaag | tggattgatg | tgatatctcc | actgacgtaa | 540 |
| gggatgacgc | acaatcccac | tatccttcgc | aagacccttc | ctctatataa | ggaagttcat | 600 |
| ttcatttgga | gaggacacgc | tgacaagctg | actctagcag | atcctctaga | accatcttcc | 660 |
| acacactcaa | gccacactat | ggagaacac | acagggacaa | cacaccataa | gatccaaggg | 720 |
| aggcctccgc | cgccgccggt | aaccaccccg | cccctctcct | ctttctttct | ccgttttttt | 780 |
| ttccgtctcg | gtctcgatct | ttggccttgg | tagtttgggt | gggcgagagg | cggcttcgtg | 840 |
| cgcgcccaga | tcggtgcgcg | ggaggggcgg | gatctcgcgg | ctgggctct | cgccggcgtg | 900 |
| gatccggccc | ggatctcgcg | gggaatgggg | ctctcggatg | tagatctgcg | atccgccgtt | 960 |
| gttgggggag | atgatggggg | gttaaaatt | tccgccgtgc | taaacaagat | caggaagagg | 1020 |
| ggaaaagggc | actatggttt | atattttat | atattctgc | tgcttcgtca | ggcttagatg | 1080 |
| tgctagatct | ttctttcttc | tttttgtggg | tagaatttga | atccctcagc | attgttcatc | 1140 |
| ggtagtttt | ctttcatga | tttgtgacaa | atgcagcctc | gtgcggagct | ttttgtagg | 1200 |

```
tagaagtgat caacc atg gac aac aac cca aac atc aac gag tgc atc ccg       1251
                Met Asp Asn Asn Pro Asn Ile Asn Glu Cys Ile Pro
                1               5                   10 tac aac tgc ctc agc aac cct gag gtc gag gtg ctc ggc ggt gag cgc        1299
Tyr Asn Cys Leu Ser Asn Pro Glu Val Glu Val Leu Gly Gly Glu Arg
    15                  20                  25 atc gag acc ggt tac acc ccc atc gac atc tcc ctc tcc ctc acg cag        1347
Ile Glu Thr Gly Tyr Thr Pro Ile Asp Ile Ser Leu Ser Leu Thr Gln
30                  35                  40 ttc ctg ctc agc gag ttc gtg cca ggc gct ggc ttc gtc ctg ggc ctc        1395
Phe Leu Leu Ser Glu Phe Val Pro Gly Ala Gly Phe Val Leu Gly Leu
45                  50                  55                  60 gtg gac atc atc tgg ggc atc ttt ggc ccc tcc cag tgg gac gcc ttc        1443
Val Asp Ile Ile Trp Gly Ile Phe Gly Pro Ser Gln Trp Asp Ala Phe
                65                  70                  75 ctg gtg caa atc gag cag ctc atc aac cag agg atc gag gag ttc gcc        1491
Leu Val Gln Ile Glu Gln Leu Ile Asn Gln Arg Ile Glu Glu Phe Ala
            80                  85                  90
```

-continued

| | | | | | | | | | | | | | | | | |
|---|---|---|---|---|---|---|---|---|---|---|---|---|---|---|---|---|
| agg | aac | cag | gcc | atc | agc | cgc | ctg | gag | ggc | ctc | agc | aac | ctc | tac | caa | 1539 |
| Arg | Asn | Gln | Ala | Ile | Ser | Arg | Leu | Glu | Gly | Leu | Ser | Asn | Leu | Tyr | Gln | |
| | 95 | | | | 100 | | | | | 105 | | | | | | |

| atc | tac | gct | gag | agc | ttc | cgc | gag | tgg | gag | gcc | gac | ccc | act | aac | cca | 1587 |
| Ile | Tyr | Ala | Glu | Ser | Phe | Arg | Glu | Trp | Glu | Ala | Asp | Pro | Thr | Asn | Pro | |
| 110 | | | | | 115 | | | | | 120 | | | | | | |

| gct | ctc | cgc | gag | gag | atg | cgc | atc | cag | ttc | aac | gac | atg | aac | agc | gcc | 1635 |
| Ala | Leu | Arg | Glu | Glu | Met | Arg | Ile | Gln | Phe | Asn | Asp | Met | Asn | Ser | Ala | |
| 125 | | | | | 130 | | | | | 135 | | | | | 140 | |

| ctg | acc | acc | gcc | atc | cca | ctc | ttc | gcc | gtc | cag | aac | tac | caa | gtc | ccg | 1683 |
| Leu | Thr | Thr | Ala | Ile | Pro | Leu | Phe | Ala | Val | Gln | Asn | Tyr | Gln | Val | Pro | |
| | | | | 145 | | | | | 150 | | | | | 155 | | |

| ctc | ctg | tcc | gtg | tac | gtc | cag | gcc | gcc | aac | ctg | cac | ctc | agc | gtg | ctg | 1731 |
| Leu | Leu | Ser | Val | Tyr | Val | Gln | Ala | Ala | Asn | Leu | His | Leu | Ser | Val | Leu | |
| | | | | 160 | | | | | 165 | | | | | 170 | | |

| agg | gac | gtc | agc | gtg | ttt | ggc | cag | agg | tgg | ggc | ttc | gac | gcc | gcc | acc | 1779 |
| Arg | Asp | Val | Ser | Val | Phe | Gly | Gln | Arg | Trp | Gly | Phe | Asp | Ala | Ala | Thr | |
| | | 175 | | | | | 180 | | | | | 185 | | | | |

| atc | aac | agc | cgc | tac | aac | gac | ctc | acc | agg | ctg | atc | ggc | aac | tac | acc | 1827 |
| Ile | Asn | Ser | Arg | Tyr | Asn | Asp | Leu | Thr | Arg | Leu | Ile | Gly | Asn | Tyr | Thr | |
| | 190 | | | | | 195 | | | | | 200 | | | | | |

| gac | cac | gct | gtc | cgc | tgg | tac | aac | act | ggc | ctg | gag | cgc | gtc | tgg | ggc | 1875 |
| Asp | His | Ala | Val | Arg | Trp | Tyr | Asn | Thr | Gly | Leu | Glu | Arg | Val | Trp | Gly | |
| 205 | | | | | 210 | | | | | 215 | | | | | 220 | |

| cct | gat | tct | aga | gac | tgg | att | cgc | tac | aac | cag | ttc | agg | cgc | gag | ctg | 1923 |
| Pro | Asp | Ser | Arg | Asp | Trp | Ile | Arg | Tyr | Asn | Gln | Phe | Arg | Arg | Glu | Leu | |
| | | | | 225 | | | | | 230 | | | | | 235 | | |

| acc | ctc | acc | gtc | ctg | gac | att | gtg | tcc | ctc | ttc | ccg | aac | tac | gac | tcc | 1971 |
| Thr | Leu | Thr | Val | Leu | Asp | Ile | Val | Ser | Leu | Phe | Pro | Asn | Tyr | Asp | Ser | |
| | | | | 240 | | | | | 245 | | | | | 250 | | |

| cgc | acc | tac | ccg | atc | cgc | acc | gtg | tcc | caa | ctg | acc | cgc | gaa | atc | tac | 2019 |
| Arg | Thr | Tyr | Pro | Ile | Arg | Thr | Val | Ser | Gln | Leu | Thr | Arg | Glu | Ile | Tyr | |
| | | 255 | | | | | 260 | | | | | 265 | | | | |

| acc | aac | ccc | gtc | ctg | gag | aac | ttc | gac | ggt | agc | ttc | agg | ggc | agc | gcc | 2067 |
| Thr | Asn | Pro | Val | Leu | Glu | Asn | Phe | Asp | Gly | Ser | Phe | Arg | Gly | Ser | Ala | |
| | 270 | | | | | 275 | | | | | 280 | | | | | |

| cag | ggc | atc | gag | ggc | tcc | atc | agg | agc | cca | cac | ctg | atg | gac | atc | ctc | 2115 |
| Gln | Gly | Ile | Glu | Gly | Ser | Ile | Arg | Ser | Pro | His | Leu | Met | Asp | Ile | Leu | |
| 285 | | | | | 290 | | | | | 295 | | | | | 300 | |

| aac | agc | atc | act | atc | tac | acc | gat | gcc | cac | cgc | ggc | gag | tac | tac | tgg | 2163 |
| Asn | Ser | Ile | Thr | Ile | Tyr | Thr | Asp | Ala | His | Arg | Gly | Glu | Tyr | Tyr | Trp | |
| | | | | 305 | | | | | 310 | | | | | 315 | | |

| tcc | ggc | cac | cag | atc | atg | gcc | tcc | ccg | gtc | ggc | ttc | agc | ggc | ccc | gag | 2211 |
| Ser | Gly | His | Gln | Ile | Met | Ala | Ser | Pro | Val | Gly | Phe | Ser | Gly | Pro | Glu | |
| | | 320 | | | | | 325 | | | | | 330 | | | | |

| ttt | acc | ttt | cct | ctc | tac | ggc | acg | atg | ggc | aac | gcc | gct | cca | caa | caa | 2259 |
| Phe | Thr | Phe | Pro | Leu | Tyr | Gly | Thr | Met | Gly | Asn | Ala | Ala | Pro | Gln | Gln | |
| | | 335 | | | | | 340 | | | | | 345 | | | | |

| cgc | atc | gtc | gct | cag | ctg | ggc | cag | ggc | gtc | tac | cgc | acc | ctg | agc | tcc | 2307 |
| Arg | Ile | Val | Ala | Gln | Leu | Gly | Gln | Gly | Val | Tyr | Arg | Thr | Leu | Ser | Ser | |
| | 350 | | | | | 355 | | | | | 360 | | | | | |

| acc | ctg | tac | cgc | agg | ccc | ttc | aac | atc | ggt | atc | aac | aac | cag | cag | ctg | 2355 |
| Thr | Leu | Tyr | Arg | Arg | Pro | Phe | Asn | Ile | Gly | Ile | Asn | Asn | Gln | Gln | Leu | |
| 365 | | | | | 370 | | | | | 375 | | | | | 380 | |

| tcc | gtc | ctg | gat | ggc | act | gag | ttc | gcc | tac | ggc | acc | tcc | tcc | aac | ctg | 2403 |
| Ser | Val | Leu | Asp | Gly | Thr | Glu | Phe | Ala | Tyr | Gly | Thr | Ser | Ser | Asn | Leu | |
| | | | | 385 | | | | | 390 | | | | | 395 | | |

| ccc | tcc | gct | gtc | tac | cgc | aag | agc | ggc | acg | gtg | gat | tcc | ctg | gac | gag | 2451 |
| Pro | Ser | Ala | Val | Tyr | Arg | Lys | Ser | Gly | Thr | Val | Asp | Ser | Leu | Asp | Glu | |
| | | 400 | | | | | 405 | | | | | 410 | | | | |

```
atc cca cca cag aac aac aat gtg ccc ccc agg cag ggt ttt tcc cac      2499
Ile Pro Pro Gln Asn Asn Asn Val Pro Pro Arg Gln Gly Phe Ser His
        415                 420                 425 agg ctc agc cac gtg tcc atg ttc cgc tcc ggc ttc agc aac tcg tcc      2547
Arg Leu Ser His Val Ser Met Phe Arg Ser Gly Phe Ser Asn Ser Ser
    430                 435                 440 gtg agc atc atc aga gct cct atg ttc tct tgg ata cac cgt agt gct      2595
Val Ser Ile Ile Arg Ala Pro Met Phe Ser Trp Ile His Arg Ser Ala
445                 450                 455                 460 gag ttc aac aac atc att gca tcc gac agc att act caa ata ccc ttg      2643
Glu Phe Asn Asn Ile Ile Ala Ser Asp Ser Ile Thr Gln Ile Pro Leu
                465                 470                 475 gtg aaa gca cat aca ctt cag tca ggt act act gtt gtc aga ggt cca      2691
Val Lys Ala His Thr Leu Gln Ser Gly Thr Thr Val Val Arg Gly Pro
            480                 485                 490 ggg ttt aca gga gga gac att ctt cgt cgc aca agt gga gga ccc ttt      2739
Gly Phe Thr Gly Gly Asp Ile Leu Arg Arg Thr Ser Gly Gly Pro Phe
        495                 500                 505 gct tac act att gtt aac atc aat ggc caa ttg ccc caa agg tat cgt      2787
Ala Tyr Thr Ile Val Asn Ile Asn Gly Gln Leu Pro Gln Arg Tyr Arg
    510                 515                 520 gca aga atc cgc tat gcc tct act aca aat ctc agg atc tac gtg act      2835
Ala Arg Ile Arg Tyr Ala Ser Thr Thr Asn Leu Arg Ile Tyr Val Thr
525                 530                 535                 540 gtt gca ggt gaa agg atc ttt gct ggt cag ttc aac aag act atg gat      2883
Val Ala Gly Glu Arg Ile Phe Ala Gly Gln Phe Asn Lys Thr Met Asp
                545                 550                 555 acc ggt gac cct ttg aca ttc caa tct ttt agc tac gca act atc aac      2931
Thr Gly Asp Pro Leu Thr Phe Gln Ser Phe Ser Tyr Ala Thr Ile Asn
            560                 565                 570 aca gct ttt aca ttc cca atg agc cag agt agc ttc aca gta ggt gct      2979
Thr Ala Phe Thr Phe Pro Met Ser Gln Ser Ser Phe Thr Val Gly Ala
        575                 580                 585 gac act ttc agc tca ggg aat gaa gtt tac atc gac agg ttt gaa ttg      3027
Asp Thr Phe Ser Ser Gly Asn Glu Val Tyr Ile Asp Arg Phe Glu Leu
    590                 595                 600 att cca gtt act gca acc ctc gag gct gag tac aac ctt gag aga gcc      3075
Ile Pro Val Thr Ala Thr Leu Glu Ala Glu Tyr Asn Leu Glu Arg Ala
605                 610                 615                 620 cag aag gct gtg aac gcc ctc ttt acc tcc acc aat cag ctt ggc ttg      3123
Gln Lys Ala Val Asn Ala Leu Phe Thr Ser Thr Asn Gln Leu Gly Leu
                625                 630                 635 aaa act aac gtt act gac tat cac att gac caa gtg tcc aac ttg gtc      3171
Lys Thr Asn Val Thr Asp Tyr His Ile Asp Gln Val Ser Asn Leu Val
            640                 645                 650 acc tac ctt agc gat gag ttc tgc ctc gac gag aag cgt gaa ctc tcc      3219
Thr Tyr Leu Ser Asp Glu Phe Cys Leu Asp Glu Lys Arg Glu Leu Ser
        655                 660                 665 gag aaa gtt aaa cac gcc aag cgt ctc agc gac gag agg aat ctc ttg      3267
Glu Lys Val Lys His Ala Lys Arg Leu Ser Asp Glu Arg Asn Leu Leu
    670                 675                 680 caa gac tcc aac ttc aaa gac atc aac agg cag cca gaa cgt ggt tgg      3315
Gln Asp Ser Asn Phe Lys Asp Ile Asn Arg Gln Pro Glu Arg Gly Trp
685                 690                 695                 700 ggt gga agc acc ggg atc acc atc caa gga ggc gac gat gtg ttc aag      3363
Gly Gly Ser Thr Gly Ile Thr Ile Gln Gly Gly Asp Asp Val Phe Lys
                705                 710                 715 gag aac tac gtc acc ctc tcc gga act ttc gac gag tgc tac cct acc      3411
Glu Asn Tyr Val Thr Leu Ser Gly Thr Phe Asp Glu Cys Tyr Pro Thr
            720                 725                 730
```

```
tac ttg tac cag aag atc gat gag tcc aaa ctc aaa gcc ttc acc agg      3459
Tyr Leu Tyr Gln Lys Ile Asp Glu Ser Lys Leu Lys Ala Phe Thr Arg
        735                 740                 745 tat caa ctt aga ggc tac atc gaa gac agc caa gac ctt gaa atc tac      3507
Tyr Gln Leu Arg Gly Tyr Ile Glu Asp Ser Gln Asp Leu Glu Ile Tyr
750                 755                 760 tcg atc agg tac aat gcc aag cac gag acc gtg aat gtc cca ggt act      3555
Ser Ile Arg Tyr Asn Ala Lys His Glu Thr Val Asn Val Pro Gly Thr
765                 770                 775                 780 ggt tcc ctc tgg cca ctt tct gcc caa tct ccc att ggg aag tgt gga      3603
Gly Ser Leu Trp Pro Leu Ser Ala Gln Ser Pro Ile Gly Lys Cys Gly
                785                 790                 795 gag cct aac aga tgc gct cca cac ctt gag tgg aat cct gac ttg gac      3651
Glu Pro Asn Arg Cys Ala Pro His Leu Glu Trp Asn Pro Asp Leu Asp
            800                 805                 810 tgc tcc tgc agg gat ggc gag aag tgt gcc cac cat tct cat cac ttc      3699
Cys Ser Cys Arg Asp Gly Glu Lys Cys Ala His His Ser His His Phe
815                 820                 825 tcc ttg gac atc gat gtg gga tgt act gac ctg aat gag gac ctc gga      3747
Ser Leu Asp Ile Asp Val Gly Cys Thr Asp Leu Asn Glu Asp Leu Gly
830                 835                 840 gtc tgg gtc atc ttc aag atc aag acc caa gac gga cac gca aga ctt      3795
Val Trp Val Ile Phe Lys Ile Lys Thr Gln Asp Gly His Ala Arg Leu
845                 850                 855                 860 ggc aac ctt gag ttt ctc gaa gag aaa cca ttg gtc ggt gaa gct ctc      3843
Gly Asn Leu Glu Phe Leu Glu Glu Lys Pro Leu Val Gly Glu Ala Leu
                865                 870                 875 gct cgt gtg aag aga gca gag aag aag tgg agg gac aaa cgt gag aaa      3891
Ala Arg Val Lys Arg Ala Glu Lys Lys Trp Arg Asp Lys Arg Glu Lys
            880                 885                 890 ctc gaa tgg gaa act aac atc gtt tac aag gag gcc aaa gag tcc gtg      3939
Leu Glu Trp Glu Thr Asn Ile Val Tyr Lys Glu Ala Lys Glu Ser Val
        895                 900                 905 gat gct ttg ttc gtg aac tcc caa tat gat cag ttg caa gcc gac acc      3987
Asp Ala Leu Phe Val Asn Ser Gln Tyr Asp Gln Leu Gln Ala Asp Thr
910                 915                 920 aac atc gcc atg atc cac gcc gca gac aaa cgt gtg cac agc att cgt      4035
Asn Ile Ala Met Ile His Ala Ala Asp Lys Arg Val His Ser Ile Arg
925                 930                 935                 940 gag gct tac ttg cct gag ttg tcc gtg atc cct ggt gtg aac gct gcc      4083
Glu Ala Tyr Leu Pro Glu Leu Ser Val Ile Pro Gly Val Asn Ala Ala
                945                 950                 955 atc ttc gag gaa ctt gag gga cgt atc ttt acc gca ttc tcc ttg tac      4131
Ile Phe Glu Glu Leu Glu Gly Arg Ile Phe Thr Ala Phe Ser Leu Tyr
            960                 965                 970 gat gcc aga aac gtc atc aag aac ggt gac ttc aac aat ggc ctc agc      4179
Asp Ala Arg Asn Val Ile Lys Asn Gly Asp Phe Asn Asn Gly Leu Ser
        975                 980                 985 tgc tgg aat gtg aaa ggt cat gtg gac gtg gag gaa cag aac aat cag      4227
Cys Trp Asn Val Lys Gly His Val Asp Val Glu Glu Gln Asn Asn Gln
990                 995                 1000 cgt tcc gtc ctg gtt gtg cct gag tgg gaa gct gaa gtg tcc caa         4272
Arg Ser Val Leu Val Val Pro Glu Trp Glu Ala Glu Val Ser Gln
1005                1010                1015 gag gtt aga gtc tgt cca ggt aga ggc tac att ctc cgt gtg acc         4317
Glu Val Arg Val Cys Pro Gly Arg Gly Tyr Ile Leu Arg Val Thr
1020                1025                1030 gct tac aag gag gga tac ggt gag ggt tgc gtg acc atc cac gag         4362
Ala Tyr Lys Glu Gly Tyr Gly Glu Gly Cys Val Thr Ile His Glu
1035                1040                1045
```

| | | | | | | | | | | |
|---|---|---|---|---|---|---|---|---|---|---|
| atc | gag | aac | aac | acc | gac | gag | ctt | aag | ttc | tcc | aac | tgc | gtc | gag | 4407 |
| Ile | Glu | Asn | Asn | Thr | Asp | Glu | Leu | Lys | Phe | Ser | Asn | Cys | Val | Glu |
| 1050 | | | | | 1055 | | | | | 1060 | | | | |

| gaa | gaa | atc | tat | ccc | aac | aac | acc | gtt | act | tgc | aac | gac | tac | act | 4452 |
| Glu | Glu | Ile | Tyr | Pro | Asn | Asn | Thr | Val | Thr | Cys | Asn | Asp | Tyr | Thr |
| 1065 | | | | | 1070 | | | | | 1075 | | | | |

| gtg | aat | cag | gaa | gag | tac | gga | ggt | gcc | tac | act | agc | cgt | aac | aga | 4497 |
| Val | Asn | Gln | Glu | Glu | Tyr | Gly | Gly | Ala | Tyr | Thr | Ser | Arg | Asn | Arg |
| 1080 | | | | | 1085 | | | | | 1090 | | | | |

| ggt | tac | aac | gaa | gct | cct | tcc | gtt | cct | gct | gac | tat | gcc | tcc | gtg | 4542 |
| Gly | Tyr | Asn | Glu | Ala | Pro | Ser | Val | Pro | Ala | Asp | Tyr | Ala | Ser | Val |
| 1095 | | | | | 1100 | | | | | 1105 | | | | |

| tac | gag | gag | aaa | tcc | tac | aca | gat | ggc | aga | cgt | gag | aac | cct | tgc | 4587 |
| Tyr | Glu | Glu | Lys | Ser | Tyr | Thr | Asp | Gly | Arg | Arg | Glu | Asn | Pro | Cys |
| 1110 | | | | | 1115 | | | | | 1120 | | | | |

| gag | ttc | aac | aga | ggt | tac | agg | gac | tac | aca | cca | ctt | cca | gtt | ggc | 4632 |
| Glu | Phe | Asn | Arg | Gly | Tyr | Arg | Asp | Tyr | Thr | Pro | Leu | Pro | Val | Gly |
| 1125 | | | | | 1130 | | | | | 1135 | | | | |

| tat | gtt | acc | aag | gag | ctt | gag | tac | ttt | cct | gag | acc | gac | aaa | gtg | 4677 |
| Tyr | Val | Thr | Lys | Glu | Leu | Glu | Tyr | Phe | Pro | Glu | Thr | Asp | Lys | Val |
| 1140 | | | | | 1145 | | | | | 1150 | | | | |

| tgg | atc | gag | atc | ggt | gaa | acc | gag | gga | acc | ttc | atc | gtg | gac | agc | 4722 |
| Trp | Ile | Glu | Ile | Gly | Glu | Thr | Glu | Gly | Thr | Phe | Ile | Val | Asp | Ser |
| 1155 | | | | | 1160 | | | | | 1165 | | | | |

| gtg | gag | ctt | ctc | ttg | atg | gag | gaa | taa | tga | gatctatcga ttctagaagg | 4772 |
| Val | Glu | Leu | Leu | Leu | Met | Glu | Glu |
| 1170 | | | | | 1175 | | | |

| cctgaattct | gcatgcgttt | ggacgtatgc | tcattcaggt | tggagccaat | ttggttgatg | 4832 |
| tgtgtgcgag | ttcttgcgag | tctgatgaga | catctctgta | ttgtgtttct | ttccccagtg | 4892 |
| ttttctgtac | ttgtgtaatc | ggctaatcgc | caacagattc | ggcgatgaat | aaatgagaaa | 4952 |
| taaattgttc | tgattttgag | tgcaaaaaaa | aaggaatt | | | 4990 |

```
<210> SEQ ID NO 8
<211> LENGTH: 1177
<212> TYPE: PRT
<213> ORGANISM: artificial
<220> FEATURE:
<223> OTHER INFORMATION: Synthetic Construct

<400> SEQUENCE: 8
```

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

-continued

```
Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525

Tyr Ala Ser Thr Thr Asn Leu Arg Ile Tyr Val Thr Val Ala Gly Glu
    530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
```

```
            565                 570                 575
Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
            595                 600                 605

Ala Thr Leu Glu Ala Glu Tyr Asn Leu Glu Arg Ala Gln Lys Ala Val
            610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                    645                 650                 655

Asp Glu Phe Cys Leu Asp Glu Lys Arg Glu Leu Ser Glu Lys Val Lys
                660                 665                 670

His Ala Lys Arg Leu Ser Asp Glu Arg Asn Leu Leu Gln Asp Ser Asn
                675                 680                 685

Phe Lys Asp Ile Asn Arg Gln Pro Glu Arg Gly Trp Gly Gly Ser Thr
            690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                    725                 730                 735

Lys Ile Asp Glu Ser Lys Leu Lys Ala Phe Thr Arg Tyr Gln Leu Arg
                740                 745                 750

Gly Tyr Ile Glu Asp Ser Gln Asp Leu Glu Ile Tyr Ser Ile Arg Tyr
                755                 760                 765

Asn Ala Lys His Glu Thr Val Asn Val Pro Gly Thr Gly Ser Leu Trp
            770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                    805                 810                 815

Asp Gly Glu Lys Cys Ala His His Ser His His Phe Ser Leu Asp Ile
                820                 825                 830

Asp Val Gly Cys Thr Asp Leu Asn Glu Asp Leu Gly Val Trp Val Ile
                835                 840                 845

Phe Lys Ile Lys Thr Gln Asp Gly His Ala Arg Leu Gly Asn Leu Glu
            850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                    885                 890                 895

Thr Asn Ile Val Tyr Lys Glu Ala Lys Glu Ser Val Asp Ala Leu Phe
                900                 905                 910

Val Asn Ser Gln Tyr Asp Gln Leu Gln Ala Asp Thr Asn Ile Ala Met
                915                 920                 925

Ile His Ala Ala Asp Lys Arg Val His Ser Ile Arg Glu Ala Tyr Leu
            930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                    965                 970                 975

Val Ile Lys Asn Gly Asp Phe Asn Gly Leu Ser Cys Trp Asn Val
                980                 985                 990
```

-continued

```
Lys Gly His Val Asp Val Glu Glu  Gln Asn Asn Gln Arg  Ser Val Leu
        995             1000                1005

Val Val Pro Glu Trp Glu Ala  Glu Val Ser Gln Glu  Val Arg Val
    1010            1015                1020

Cys Pro Gly Arg Gly Tyr Ile  Leu Arg Val Thr Ala  Tyr Lys Glu
    1025            1030                1035

Gly Tyr Gly Glu Gly Cys Val  Thr Ile His Glu Ile  Glu Asn Asn
    1040            1045                1050

Thr Asp Glu Leu Lys Phe Ser  Asn Cys Val Glu Glu  Glu Ile Tyr
    1055            1060                1065

Pro Asn Asn Thr Val Thr Cys  Asn Asp Tyr Thr Val  Asn Gln Glu
    1070            1075                1080

Glu Tyr Gly Gly Ala Tyr Thr  Ser Arg Asn Arg Gly  Tyr Asn Glu
    1085            1090                1095

Ala Pro Ser Val Pro Ala Asp  Tyr Ala Ser Val Tyr  Glu Glu Lys
    1100            1105                1110

Ser Tyr Thr Asp Gly Arg Arg  Glu Asn Pro Cys Glu  Phe Asn Arg
    1115            1120                1125

Gly Tyr Arg Asp Tyr Thr Pro  Leu Pro Val Gly Tyr  Val Thr Lys
    1130            1135                1140

Glu Leu Glu Tyr Phe Pro Glu  Thr Asp Lys Val Trp  Ile Glu Ile
    1145            1150                1155

Gly Glu Thr Glu Gly Thr Phe  Ile Val Asp Ser Val  Glu Leu Leu
    1160            1165                1170

Leu Met Glu Glu
    1175
```

NUCLEOTIDE SEQUENCES ENCODING INSECTICIDAL PROTEINS

This application is a §371 national phase of PCT application PCT/US2006/033868, filed 30 Aug. 2006, which claims benefit of 60/713,144, filed 31 Aug. 2005.

BACKGROUND OF THE INVENTION

The present invention provides novel coding sequences for use in plants. The coding sequences encode a chimeric insecticidal protein toxic to a wide range of lepidopteran species crop pests.

Commercial formulations of naturally occurring *B. thuringiensis* isolates have long been used for the biological control of agricultural insect pests. Bt spores and crystals obtained from fermentation of *Bacillus thuringiensis* species are concentrated and formulated for foliar application according to conventional agricultural practices.

Members of the family of Cry1 crystal proteins are known to exhibit bioactivity against lepidopteran insect larvae and are useful as agents for controlling lepidopteran insect pests. The precursor form of Cry1 δ-endotoxins consist of two approximately equal sized segments. The carboxy-terminal portion of the precursor protein, or pro-toxin segment, stabilizes crystal formation and exhibits no insecticidal activity. The amino-terminal half of the precursor protein comprises the toxin segment of the Cry1 protein and, based on alignment of conserved or substantially conserved sequences within Cry1 family members, can be further sub-divided into three structural domains. These three sub-domains are based on a three dimensional crystallographic structural model of a Cry1A δ-endotoxin in which the three sub-domains were referred to as Domain I, Domain II, and Domain III, respectively as measured from the amino terminus of the protein toxin segment. Domain I comprises about the first third of the active toxin segment and has been shown to be essential for channel formation (Thompson et al., 1995). Domains II and III respectively comprise about the central and carboxy-terminal segments of the active toxin portion. Domains II and III have both been implicated in receptor binding and insect species specificity, depending on the insect and δ-endotoxin being examined (Thompson et al., 1995).

The likelihood of arbitrarily creating a chimeric protein with enhanced properties from the reassortment of the domain structures of the numerous native insecticidal crystal proteins known in the art is remote. This is a result of the complex nature of protein structure, folding, oligomerization, and activation including correct proteolytic processing of the chimeric precursor, if expressed in such form, to release an insecticidal toxin segment. Only by careful selection of specific target regions within each parental protein for inclusion into a chimeric structure can functional insecticidal toxins be constructed that exhibit improved insecticidal activity in comparison to the parental proteins from which the chimeras are derived. Experience has shown that reassembly of the toxin domains, i.e., assembly of a chimeric toxin consisting of domain I, II, and III of any two or more toxins that are different from each other, results in the construction of a protein that exhibits faulty crystal formation and/or the complete lack of any detectable insecticidal activity directed to a preferred target insect pest species. In some instances, a chimeric toxin will exhibit good crystal formation properties, yet exhibit no detectable insecticidal activity. Only by trial and error are effective insecticidal chimeras formulated, and even then, the skilled artisan is not certain to end up with a chimera that exhibits insecticidal activity that is equivalent to or improved in comparison to any single parental toxin protein from which the constituents of the chimera may have been derived.

The literature reports examples of the construction or assembly of chimeric proteins from two or more Bt insecticidal crystal protein precursors, yet not all exhibited insecticidal or crystal forming properties that were equivalent to or improved in comparison to the precursor proteins from which the chimeras were derived. (Bosch et al. (WO95/06730); Thompson et al. (WO95/30753); Thompson et al. (WO95/30752); Malvar et al. (WO98/22595); Gilroy et al. (U.S. Pat. No. 5,128,130); Gilroy (U.S. Pat. No. 5,055,294); Lee et al. (1992) Gene 267:3115-3121; Honee et al. (1991) Mol. Microbiol. 5:2799-2806; Schnepf et al. (1990) J. Biol. Chem. 265:20923-20930; Perlak et al. (1990) Bio/Technol. 8:939-9943; Perlak et al (1993) Plant Mol. Biol. 22:313-321).

Expression of *B. thuringiensis* δ-endotoxins in transgenic corn plants has proven to be an effective means of controlling agriculturally important insect pests (Perlak et al. 1990; 1993). Transgenic crops expressing *B. thuringiensis* δ-endotoxins enable growers to significantly reduce the time and costs associated with applications of topically applied chemical insecticides. Use of transgenes encoding *B. thuringiensis* δ-endotoxins is particularly advantageous. Crop plants expressing *B. thuringiensis* δ-endotoxins in areas under heavy insect pressure exhibit improved yields that are better than otherwise similar non-transgenic commercial plant varieties. However, it is anticipated that insects may evolve resistance to *B. thuringiensis* δ-endotoxins expressed in transgenic plants. Such resistance, should it become widespread, would clearly limit the commercial value of germplasm containing genes encoding such *B. thuringiensis* δ-endotoxins. One possible way of increasing the effectiveness of the transgenic insecticides against target pests and contemporaneously reducing the development of insecticide-resistant pests would be to ensure that transgenic crops express high levels of *B. thuringiensis* δ-endotoxins (McGaughey and Whalon 1993; Roush 1994). In addition, having a repository of insecticidal genes that are effective against groups of insect pests and which manifest their effects through different modes of action can safeguard against any development of resistance. Expression in a plant of two or more insecticidal compositions toxic to the same insect species, each insecticide being expressed at levels high enough to effectively delay the onset of resistance, would be another way to achieve control of the development of resistance. Examples of such insecticides useful in such combinations include but are not limited to Bt toxins, *Xenorhabdus* sp. or *Photorhabdus* sp. insecticidal proteins, deallergenized and de-glycosylated patatin proteins and/or permuteins, plant lectins, and the like. Achieving co-expression of multiple insecticidally active proteins in the same plant, and/or high expression levels of those insecticidal proteins without causing undesirable plant morphological effects has been elusive.

Only a handful of the more than two-hundred and fifty individual insecticidal proteins that have been identified from *Bacillus thuringiensis* species have been tested for expression in plants. Several Cry1's, Cry3's, Cry2Aa and Cry2Ab, binary toxins Cry33/34 and Cry23/37, and a Cry9 have been successfully expressed in plants. Cry1 proteins represent the largest class of proteins that have been expressed in plants, but none have been expressed at high levels. It was necessary to target the Cry2Ab to the chloroplast to avoid undesirable phytotoxic effects. The majority of acres planted in recombinant plants express Cry1A proteins. The likelihood of the onset of resistance to Cry1A proteins by targeted insect pest species is substantially higher than it would be if a resistance management allele was also expressed along with the cry1 allele, or if the cry1 allele was expressed at high levels. Therefore it is desirable that alternative toxin genes be developed for expression in plants as supplements and replacements for those being used presently in the first and second generations of transgenic insect resistant plants.

SUMMARY OF THE INVENTION

The invention provides isolated nucleotide sequences for expression in plants encoding an insecticidal protein exhibiting lepidopteran insect inhibitory properties. SEQ ID NO:1 is an example of such nucleotide sequences consisting of a cry1A.105 gene and encodes an insect inhibitory Cry1A.105 protein. SEQ ID NO:1 is similar to SEQ ID NO:3, both encoding a Cry1A.105 protein. SEQ ID NO: 1 is preferred for use in a dicotyledonous cells, while SEQ ID NO:3 is preferred for use in monocotyledonous cells. SEQ ID NO:4 is encoded from SEQ ID NO:3 and is identical in amino acid sequence to SEQ ID NO:2. The isolated nucleotide sequence is intended to include sequences that exhibit at least from about 88% to about 90% or greater nucleotide sequence identity to the sequence as set forth at SEQ ID NO:1, or that hybridize to SEQ ID NO:1 under stringent hybridization conditions. The isolated nucleotide sequence is also intended to include sequences that exhibit at least about 90% nucleotide sequence identity to the sequence as set forth at SEQ ID NO:3, or that hybridize to SEQ ID NO:3 under stringent hybridization conditions.

The invention also provides an isolated and purified insecticidal protein exhibiting inhibitory activity directed to lepidopteran insect species. The insecticidal protein is designated herein at least as the toxin portion of Cry1A.105 and exhibits an amino acid sequence as set forth in SEQ ID NO:2. The full length precursor protein consisting of about 1177 amino acids as set forth in SEQ ID NO:2 is also referred to as an insecticidal Cry1A.105 protein, however any fragment of the precursor protein that exhibits insecticidal bioactivity is intended to be referred to as an insecticidal Cry1A.105 protein, and includes at least a Cry1A.105 insecticidal protein corresponding to an amino acid sequence segment from about amino acid 1 through about amino acid 612 as set forth in SEQ ID NO:2, and may also include a segment from about amino acid 2 through about amino acid 610. Any composition consisting of an insecticidally effective amount of the insecticidal protein is intended to be within the scope of the invention.

The invention also provides an expression cassette for use in expressing an insecticidal protein as set forth in SEQ ID NO:2 in a host cell. The expression cassette preferably contains a promoter functional in the intended host cell which is linked to and regulates the expression of a nucleotide sequence encoding an insecticidal segment of a Cry1A.105 protein. Exemplary expression cassettes are provided herein as set forth at SEQ ID NO:5 and SEQ ID NO:7, intended for use in a dicot plant cell or a monocot plant cell, respectively. The promoter and the coding sequence are operably linked and function together in the host cell. The expression cassette can be intended for use in any host cell, but is preferably for use in a bacterial cell, a fungal cell, a mammalian cell, or a plant cell. Bacterial cells are preferably selected from the group consisting of a *Bacillus* species cell, a *Enterobacteriacae* species cell, a *Pseudomonas* species cell, a *Clostridium* species cell, and a *Rhizobium* species cell, and a *Agrobacterium* species cell. If the host cell is a plant cell, it is preferable that it is a cell chosen from a crop species of plant cell, preferably either a dicotyledonous plant or a monocotyledonous plant cell. Examples of dicotyledonous plant cells are alfalfa, apple, apricot, asparagus, bean, berry, blackberry, blueberry, canola, carrot, cauliflower, celery, cherry, chickpea, citrus tree, cotton, cowpea, cranberry, cucumber, cucurbit, egg plant, fruit tree, grape, lemon, lettuce, linseed, melon, mustard, nut bearing tree, okra, orange, pea, peach, peanut, pear, plum, potato, soybeans, squash, strawberry, sugar beet, sunflower, sweet potato, tobacco, tomato, turnip, and vegetable. Monocotyledonous plant cells examples are corn, wheat, oat, rice, sorghum, milo, buckwheat, rye, grass (fescue, timothy, brome, orchard, St. Augustine, Bermuda, bentgrass), and barley. Expression cassettes intended for use in a plant cell typically contain in operable linkage sequences that regulate the levels and efficiencies of expression of an intended substance, such as a Cry1A.105 insecticidal protein. Such sequences may be an expression enhancer sequence, an untranslated leader sequence, an intron sequence, a chloroplast targeting peptide encoding sequence, and a transcription termination and polyadenylation sequence.

The expression cassette is preferably incorporated into a vector for use in stabilizing the maintenance of the Cry1A.105 coding sequence within the host cell. A vector can be any number of structures known in the art, but is typically a plasmid or replicon into which the expression cassette is constructed or inserted prior to incorporation into the host cell. A vector is intended to include but not be limited to a plasmid, a cosmid, a bacmid, a phagemid, a YAC, a BAC, a suicide vector, an insertion sequence, a transposon, or even a linear nucleotide sequence to which the expression cassette is linked or in which the expression cassette is embedded.

Transgenic plants resistant to lepidopteran insect infestation are an embodiment of the present invention. Such plants contain a nucleotide sequence that encodes a Cry1A.105 insecticidal protein as set forth in SEQ ID NO:2 at least from about amino acid 2 to about amino acid 612. The transgenic plant is effective in controlling lepidopteran insect infestations brought about by insects such as leaf rollers, cutworms, armyworms, borers, bagworms, and any forage feeder. Preferred pests are fall armyworms, European corn borers, corn earworms (cotton bollworms), southwestern corn borers, and black cutworms. The present invention is intended to include the progeny and seed or fruits or product yielded from the transgenic plant of the present invention, so long as the nucleotide sequence of the present invention encoding a Cry1A.105 insecticidal segment is maintained within the heritable and/or plastid genome of the cells of the plant, its progeny, seed, and the like.

The present invention also provides one or more methods for controlling lepidopteran insect infestation of a plant by providing in the diet of an insect pest a composition that contains an insecticidally effective amount of an insecticidal Cry1A.105 protein. One such composition would be plant cells that have been or are descended from a plant cell transformed with a nucleic acid sequence that encodes an insecticidal segment of a Cry1A.105 amino acid sequence as set forth in SEQ ID NO:2. A transgenic plant generated from a plant cell transformed to contain an expression cassette, exemplified as set forth at SEQ ID NO:5 and SEQ ID NO:7, which contains a sequence encoding a Cry1A.105 insecticidal amino acid sequence, would be one means for providing an insecticidal composition in the diet of the insect. Another means would be to produce an insecticidally effective amount of a Cry1A.105 protein in a bacterial or fungal cell and provide the bacterial cell or fungal cell or a purified amount of the Cry1A.105 protein in the diet of one or more target insect pests susceptible to the Cry1A.105 protein.

A method of identifying a nucleotide sequence encoding a Cry1A.105 amino acid sequence in a biological sample is provided. The method consists of contacting a sample being tested for the presence of the Cry1A.105 coding sequence with a polynucleotide probe that binds with specificity to the Cry1A.105 coding sequence. In particular, the probe sequence binds, or hybridizes to, a Cry1A. 105 coding sequence under stringent hybridization conditions. Detecting binding in a reaction mix is diagnostic for the presence of the Cry1A.105 coding sequence.

A method of identifying an insecticidal fragment of a Cry1A.105 protein in a sample is also provided. The method consists of contacting a sample being tested for the presence of a Cry1A.105 insecticidal fragment with an antibody that binds specifically to the insecticidal fragment. Detecting the binding in a reaction mix is diagnostic for the presence of the Cry1A.105 protein in the sample.

Chimeric or hybrid insecticidal proteins are also provided. Such hybrids are composed of two or more different insecticidal proteins, each of which exhibits insecticidal activity directed to at least one member of the same insect species. The hybrid insecticidal protein is made up of parts of each of the different insecticidal proteins. Segments of insecticidal proteins used in constructing the hybrid consist of from at least about 50 to at least about 200 contiguous amino acids selected from the contiguous amino acids making up any one of the different insecticidal proteins. A Cry1A.105 insecticidal protein as set forth in SEQ ID NO:2 from about amino acid position 2 through about amino acid position 612 is intended to be included within the group of the different insecticidal proteins from which a segment may be selected for constructing a hybrid insecticidal protein.

Various advantages and features of the present invention being apparent, the nature of the invention may be more clearly understood by reference to the following detailed description, the examples, and to the appended claims.

BRIEF DESCRIPTION OF THE SEQUENCES

SEQ ID NO:1 is a synthetic sequence for expression of a Cry1A.105 insecticidal protein, preferably in a dicot cell.

SEQ ID NO:2 is a Cry1A.105 protein encoded from the nucleotide sequence as set forth at SEQ ID NO:1.

SEQ ID NO:3 is a synthetic sequence for expression of a Cry1A.105 insecticidal protein, preferably in a monocot cell.

SEQ ID NO:4 is a Cry1A.105 protein encoded from the nucleotide sequence as set forth at SEQ ID NO:3.

SEQ ID NO:5 represents a nucleotide sequence consisting of an expression cassette that functions in a plant cell, and preferably in a dicot plant cell, for expressing a Cry1A.105 insecticidal protein.

SEQ ID NO:6 represents a Cry1A.105 insecticidal protein encoded by a segment within the expression cassette as set forth in SEQ ID NO:5.

SEQ ID NO:7 represents a nucleotide sequence consisting of an expression cassette that functions in a plant cell, and preferably in a monocot plant cell, for expressing a Cry1A.105 insecticidal protein.

SEQ ID NO:8 represents a Cry1A.105 insecticidal protein encoded by a segment within the expression cassette as set forth in SEQ ID NO:7.

DETAILED DESCRIPTION OF THE INVENTION

In accordance with the present invention, the inventors have constructed nucleotide sequences that encode a novel insecticidal protein identified herein as a Cry1A.105 protein.

It has been identified that the Cry1A.105 amino acid sequence, set forth in SEQ ID NO:2, exhibits properties that provide advantages over naturally occurring Bt insecticidal proteins that are toxic to lepidopteran insect species. In particular, the Cry1A.105 protein can be expressed at high levels in both monocot and dicot plants without most transgenic events exhibiting phytotoxic effects as a result of the increased levels of expression compared to effects observed when naturally occurring Cry1 proteins are expressed in plants. In addition, the Cry1A.105 protein form stable crystals when expressed in *Bacillus thuringiensis*, likely because of the stabilizing effect of the Cry1Ac protoxin segment linked to the toxin moiety of the chimeric Cry1A.105 protein. In addition, the Cry1A.105 insecticidal protein exhibits a range of insecticidal bioactivity directed to lepidopteran species that is not observed with other naturally occurring Cry1 proteins that have been identified to date. Therefore, expression of the Cry1A.105 protein in transgenic plants results in increased numbers of morphologically normal transgenic events expressing higher levels of an analogue of a Cry1 toxin that exhibits a broad range of control of lepidopteran insect pest species for any event that is selected for commercial development. Such events should result in the advantage of delaying the onset of resistance to the Cry1A toxin analogue, and when combined with a second toxin that is toxic to one or more of the insect pest species to which the Cry1A analogue is also toxic and that exerts its mode of action in a way that is different from that of the Cry1A analogue, any likelihood of the development of resistance to either toxin is anticipated to be extremely remote.

The inventors have constructed at least two different nucleotide sequences for use in plants, each nucleotide sequence encoding the same Cry1A.105 insecticidal protein. The first (or amino terminal) about two thirds of the insecticidal portion of the Cry1A.105 protein consists of amino acid sequences derived from a Cry1Ab amino acid sequence. This sequence is linked to the carboxy-terminus of the toxin portion and a part of the protoxin domain of an amino acid sequence derived from an insecticidal Cry1 protein obtained from an Ecogen Bt aizawai strain EG6346 (Chambers et al., 1991, J. Bacteriol. 173:3966-3976). The Cry1A.105 toxin segment is linked then to a segment that is substantially a Cry1Ac protoxin peptide sequence. The inventors demonstrated that this construction provides a unique amino acid sequence that exhibits surprisingly improved insecticidal properties when compared to the properties exhibited by the protein from which the chimera is derived. Furthermore, the Cry1A.105 precursor protein exhibits excellent crystal forming properties and is efficiently solubilized and processed to the active toxin form in the gut of specific targeted lepidopteran insect pests.

The nucleotide sequences embodied herein have been constructed using methods set forth in U.S. Pat. Nos. 5,500,365, and 5,689,052, in particular by avoiding certain inimical sequences in the coding sequence that have been observed to be problematic for expression of heterologous gene sequences in plant cells. The segment encoding the toxin portion of the Cry1A.105 protein consists of nucleotides as set forth in SEQ ID NO:1 and SEQ ID NO:3 from about position 1 through about position 1830, more or less. The sequence as set forth at SEQ ID NO: 1 was constructed for use in dicotyledonous plant species, and in particular, in cotton plants. The sequence as set forth at SEQ ID NO:3 was constructed for expression in monocotyledonous plants, and in particular, in maize or corn plant species.

Nucleotide sequences of the present invention exhibit an overall identity of about 94.3% to each other and are identical from about nucleotide position 1330 through about nucleotide position 3534. The segment of each of these nucleotide sequences encoding the toxin portion of the Cry1A.105 protein exhibits, from about nucleotide position 1 through about nucleotide position 1830, about 88.9% identity to each other. The segment of these nucleotide sequences encoding the first two domain structures of the Cry1A.105 protein is substantially more diverse and exhibits only about 84.7% identity to each other.

The inventors have constructed transgenic plant events using these sequences.

SEQ ID NO: 1 was introduced into a plasmid vector containing an expression cassette consisting of a enhanced Figwort Mosaic Virus promoter (eFMV) sequence operably linked to a *Petunia hybrida* Hsp70 untranslated leader sequence (Ph.Hsp70, a.k.a., DnaK), an *Arabidopsis thaliana* ribulose bis phosphate carboxylase small subunit chloroplast targeting peptide coding sequence, and a *Pisum sativum* E9 ribulose bis phosphate carboxylase small subunit gene transcription termination and polyadenylation sequence. The Cry1A.105 coding sequence as set forth at SEQ ID NO: 1 was inserted into this expression cassette in frame with and immediately adjacent to the 3' end coding sequence of the targeting peptide coding sequence, and upstream of the E9 termination sequence. The nucleotide sequence of the resulting expression cassette is set forth at SEQ ID NO:5. A segment of the vector containing the Cry1A.105 expression cassette linked to a second expression cassette containing a plant expressible GUS marker was excised and used to generate transgenic cotton events using biolistic methods. Transgenic events were tested in bioassay for insecticidal activity against several different lepidopteran pest species and were determined to exhibit significantly better insect controlling properties than previously existing insect resistant cotton plants containing only Cry1Ac or a combination of Cry1Ac and Cry2Ab proteins. In addition, some of the Cry1A.105 transgenic cotton events exhibited levels of Cry1A.105 protein accumulation exceeding 10 to 20 parts per million throughout the growing season, even in cotton bolls, and without exhibiting any phytotoxic effects on the plant or reproductive tissues. This is in contrast to other Cry1 proteins that have been tested previously, which generally were only capable of levels of accumulation to less than about 10 parts per million, whether or not targeted to the chloroplast. Phytotoxic effects were observed when other Cry1 type proteins were tested in cotton, especially when levels of Cry1 accumulation approached or exceeded about 10 ppm.

SEQ ID NO:3 was introduced into a plasmid vector containing an expression cassette consisting of a enhanced Cauliflower Mosaic Virus promoter (eCaMV) sequence operably linked to a *Triticum aestivum* major chlorophyll a/b binding protein gene untranslated leader sequence and an *Oryza sativa* actin intron sequence, and a *Triticum aestivum* hsp17 gene transcription termination and polyadenylation sequence. The Cry1A.105 coding sequence as set forth at SEQ ID NO:3 was inserted into this expression cassette immediately adjacent to and 3' of the intron sequence and upstream of the termination sequence. The nucleotide sequence of the resulting expression cassette is set forth at SEQ ID NO:7. The vector also contains a glyphosate herbicide selectable marker that was used to select events transformed with the Cry1A.105 expression cassette. Maize events selected after transformation with the Cry1A.105 expression cassette were tested in bioassays against several lepidopteran pest species and determined to exhibit a wide range of insecticidal activity that was not prevalent with events transformed with other Bt insecticidal proteins such as Cry1Ab. The fall armyworm and black cutworm activities exhibited by events expressing insecticidal levels of Cry1A.105 coupled with the Cry1A.105 insecticidal activity directed to corn earworm and corn borer equivalent to or greater than that of events expressing Cry1Ab, provides a broader spectrum of insecticidal activity for Cry1A.105 events.

The nucleotide sequences of the present invention are exemplary. Other nucleotide sequences are capable of expressing a Cry1A.105 insecticidal protein fragment in a plant cell, and still other nucleotide sequences are capable of being designed that express well in other types of host cells. Without limiting the scope of the disclosure, it is intended that a nucleotide sequence for use in expression of a Cry1A.105 insecticidal fragment exhibit at least about 85%, or at least about 90%, or at least about 95%, or at least about 99% or greater nucleotide sequence identity to the nucleotide sequences exemplified herein. Other nucleotide sequences intended for expression of a Cry1A.105 insecticidal fragment in a host cell other than a plant cell can be of any percentage identity or similarity to the exemplified nucleotide sequences. Nucleotide sequences can vary because of the redundancy of the genetic code, and so it is possible to synthesize any number of nucleic acid sequences that encode any part of the amino acid sequence set forth in SEQ ID NO:2, and all of these sequences are intended to be within the scope of the present invention. Any isolated and purified nucleic acid sequence encoding at least an insecticidal fragment of a Cry1.105 protein is intended to be within the scope of the disclosure, as well as any composition in which the nucleic acid can be detected by antibody, by nucleic acid probe, or by one or more pairs of primers designed to produce an amplicon consisting of such sequence.

The nucleic acid sequence exemplified herein and expressed in maize consists only of a Cry1A.105 precursor protein coding sequence, while the sequence expressed in cotton consists of a chloroplast targeted Cry1A.105 precursor protein coding sequence. The expression of Cry1 proteins in plants has proven to be problematic. It is not known whether or if any particular Cry1 protein will be expressed well in any particular plant, and so trial and error experimentation is required. Some Cry1 proteins expressed in corn will result in phytotoxic effects, and so targeting the protein to the chloroplast sometimes alleviates such effects. Similar circumstances are observed with cotton plant expression of Cry1 proteins. The examples herein are not intended to teach that Cry1A.105 expression is only possible in maize if localized to the cytoplasmic space, and similarly, are not intended to teach that Cry1A.105 expression is only possible in cotton if localized to the plastid. The examples are intended to teach that either method of protein localization functions with this protein to achieve morphologically normal plants that exhibit high levels of Cry1A.105 protein expression and accumulation, and that exhibit commercial levels of resistance to a broad range of Lepidopteran insect plant pests in the genus' selected from the groups consisting of *Anticarsia, Pseudoplusia, Rachiplusia, Helicoverpa, Heliothis, Spodoptera, Epinotia,* and *Armigera*. It is believed that any plastid targeting peptide coding sequence would function effectively for directing the precursor Cry1A.105 protein to the plastid/chloroplast.

Untranslated leader sequences, introns and 3' transcription termination and polyadenylation sequences are known in the art, and the skilled artisan would understand that in certain circumstances, expression can be enhanced or stabilized by incorporating these sequences into the expression cassettes. A number of such sequences are known in the art and are intended to be included within the scope of the present disclosure. Similarly, promoters that function to achieve the regulated expression of a linked sequence are known in the art and are also intended to be included within the scope of the present disclosure. Promoters can be selected for use to drive expression of a linked sequence in any number of combinations of parameters, including but not limited to temporal control of expression, spatial or tissue specific control of expression, and to control the amount of a particular gene product desired to be accumulated within a particular plant cell or tissue.

The isolated and purified protein comprising an insecticidal fragment of the Cry1A.105 amino acid sequence is also intended to be within the scope of the present invention. Variants are also intended to be within the scope of the invention so long as the amino acid substitution or substitutions effecting the variation are generally conservative with respect to the substituted amino acid(s), and the substitution(s) does not result in a reduction of insecticidal bioactivity or range of species specificity. It is intended that an insecticidal fragment of a Cry1A.105 protein is a segment of the amino acid sequence as set forth in SEQ ID NO:2 from about amino acid position 1 through about amino acid position 650, or from about amino acid position 2 through about amino acid position 612, or from about amino acid position 5 through about amino acid position 610, or from about amino acid position 10 through about amino acid position 600. Alternatively, it is intended that an insecticidal fragment of a Cry1A.105 protein consist of from about 550 to about 650 contiguous amino acids selected from the group consisting of amino acid residues 1 through about 650 as set forth at SEQ ID NO:2. The full length precursor protein, consisting of amino acid residue 1 through about residue 3534, exhibits excellent crystal formation properties and is tolerated well by both monocot and dicot plant species. The precursor protein also exhibits excellent stability when in crystalline form, and also exhibits excellent solubility at alkaline pH, in particular alkaline pH within a range of from about 8.0 to about 12.0, or from about 8.5 to about 11.5, or from about pH 9.0 to about pH 11.0.

The protein of the present invention can be purified and used alone in an insecticidally effective amount in any number of compositions intended for use as a lepidopteran pest control agent, or can be combined in an insecticidally effective amount with any number of other pesticidal agents that are different from the Cry1A.105 protein. Such other pesticidal agents are intended to include but not to be limited to other Bt Cry or other insecticidal compositions whether or not toxic to a lepidopteran species including chemical insecticides, fungicidal or fungistatic agents, antibiotics, antibacterial agents, bacteriostatic agents, and nematicidal or nematostatic agents. Such pesticidal combinations including a Cry1A.105 along with any number of other pesticidal agents can be produced by a transgenic cell, or formulated using purified or substantially purified pesticidal agents into a pesticide composition in a form consisting of a dust, a granular material, an oil suspension, a water suspension, a mixture of oil and water emulsion, or a wettable powder, and then provided in a an agriculturally acceptable carrier for foliar applications. The compositions can be formulated into a seed treatment as well, either together with a Cry1A.105 in the composition intended for inclusion in the seed treatment, or as a composition applied to a seed that is derived from a transgenic plant transformed to express insecticidally effective amounts of a Cry1A.105, so that the seed treatment composition containing pesticidal agents is provided to a target lepidopteran pest along with cells of a plant grown from the seed that are producing pesticidally effective amounts of a Cry1A.105 protein. A combination of insecticidal proteins the each are toxic to the same insect species and yet manifest their toxicity effects through different modes of action would be a particularly useful combination of pesticidal agents for controlling lepidopteran species or delaying the onset of resistance to any single pesticidal agent otherwise effective against a particular lepidopteran species. An exemplary combination of such proteins would be a Cry1A.105 protein of the present invention, i.e., a first insecticidal protein, coupled with at least a second insecticidal protein different from the first. Such different insecticidal proteins include but are not limited to other lepidopteran Bt. crystalline proteins (other Cry1's, Cry2's, Cry5's, Cry9's), VIP proteins, lepidopteran insecticidal proteins referred to as TIC proteins, and insecticidal proteins produced by *Xenorhabdus* and *Photorhabdus* species of bacteria. Providing in the diet of an insect pest a combination of one or more insecticidal proteins along with an agent designed for achieving dsRNA mediated gene suppression of one or more genes essential for insect survival is a particularly useful combination of pesticidal agents for controlling lepidopteran species or delaying the onset of resistance to any single pesticidal agent otherwise effective against a particular lepidopteran species.

Plants transformed with the nucleotide sequences of the present invention are provided as another embodiment of the present invention. Methods for stably introducing DNA into plant cells is known in the art, and includes but is not limited to vacuum infiltration, *Agrobacterium* or *Rhizobium* mediated transformation, electroporation, and various ballistic methods. DNA introduced into plants is generally targeted for insertion into the nuclear chromosome, although insertion into the chloroplast or plastid DNA can be achieved. DNA introduced into plants is generally linked to or associated with a sequence that provides a means for identifying or selecting the cell or cells that have been stably transformed with the DNA of interest, including but not limited to scoreable markers such as fluorescence or light emitting genes and genes encoding pigments or enzymes that, in the presence of the appropriate substrate, impart a colorimetric feature to the transformed cell or cells, or by including selectable markers that allow a positive selection of transformed cells and tissue, providing a growth advantage to the transformed cells and essentially causing the non-transformed cells or tissue to become static or to die. Such selectable markers include but are not limited to genes encoding basta, bar, methotrexate resistance, neomycin phosphotransferase, glyphosate insensitive EPSPS enzymes, glyphosate oxidoreductase (GOX) enzymes, *E. coli* phnO or its equivalent, and the like.

Vectors and other types of sequences designed for maintaining, manipulating, and/or shepherding the exemplified nucleotide sequences while being manipulated in the laboratory or for introduction into a host cell are also included within the scope of the invention, and are intended to include but not be limited to phages, plasmids, bacmids, yacmids, cosmids, and the like.

Transformed plants are also within the scope of the present invention. Plants transformed to contain a nucleotide sequence encoding at least an insecticidal fragment of a Cry1A.105 protein are specifically enabled by the present disclosure. Both monocot and dicot plants are envisioned to be within the scope of the present invention. Monocots are intended to include but not be limited to corn, wheat, oat, rice, sorghum, milo, buckwheat, rye, grass (fescue, timothy, brome, orchard, St. Augustine, Bermuda, bentgrass), and barley, and dicot plants are intended to include at least alfalfa, apple, apricot, asparagus, bean, berry, blackberry, blueberry, canola, carrot, cauliflower, celery, cherry, chickpea, citrus tree, cotton, cowpea, cranberry, cucumber, cucurbit, egg plant, fruit tree, grape, lemon, lettuce, linseed, melon, mustard, nut bearing tree, okra, orange, pea, peach, peanut, pear, plum, potato, soybeans, squash, strawberry, sugar beet, sunflower, sweet potato, tobacco, tomato, turnip, and vegetable. Produce from these plants as well as seeds and tissues produced from these plants are specifically included within the present invention, so long as the seed, tissue, or produce contains a transgene encoding an insecticidal fragment of a Cry1A.105 protein.

Methods for detecting, in a biological sample, a Cry1A.105 protein or a nucleotide sequence encoding an insecticidal fragment of a Cry1A.105 protein are provided by the present invention. Cry1A.105 can be used to immunize animals to produce antibodies specific for Cry1A.105 epitopes. Cry1A.105 specific antibodies can be used to detect the presence of Cry1A.105 in a biological sample. Methods for detecting the binding of an antibody to an antigen are known in the art. Detecting the binding of an antibody to a Cry1A.105 epitope in a biological sample is diagnostic for the presence of the protein in the sample.

Nucleotide sequences encoding a Cry1A.105 insecticidal fragment can be detected as well. Synthetic nucleotide probes can be used to bind to a target sequence, i.e., a nucleotide sequence encoding a Cry1A.105 insecticidal fragment. Methods for detecting the binding of a probe to a target sequence are known in the art. Detecting the binding of a probe to the target Cry1A.105 coding sequence is diagnostic for the presence of the coding sequence in the sample.

Synthetic nucleotide primers can be used in thermal amplification reactions to produce an amplicon from a biological sample suspected of containing a nucleotide sequence encoding an insecticidal fragment of a Cry1A.105 protein. The presence of an amplicon produced in such a thermal amplification reaction is diagnostic for the presence of the nucleotide sequence in the sample. Particularly useful sequences as probes which are diagnostic for detecting the presence of the Cry1A.105 coding sequences of the present invention in a biological sample are sequences that correspond to or are perfectly complementary to (1) nucleotide position 1401-1420 as set forth at SEQ ID NO:1 or SEQ ID NO:3, or (2) nucleotide position 1821-1840 as set forth at SEQ ID NO:1 or SEQ ID NO:3. These sequences correspond to (1) the 20 nucleotides spanning the sequence encoding the junction between Domain II and Domain III of the segments of different insecticidal proteins used for constructing the insecticidal portion of the proteins of the present invention, and (2) the 20 nucleotides spanning the sequence encoding the junction between Domain III and the protoxin coding segment of the different protein coding segments used for constructing the coding sequence of the pre-pro-toxin Cry1Ab.105 protein. Nucleotide sequences that are, or are complementary to, either of these segments of DNA (1401-1420 or 1821-1840) can be used as probes for detecting the presence of these coding sequences in biological samples. The detecting of such binding is diagnostic for the presence of such coding sequences in a biological sample. Other sequences as will be recognized by the skilled artisan that flank either side of these segments of DNA can be used as primers for amplifying various sized amplicon segments from such biological samples, and such amplicons are diagnostic for the presence of such coding sequences in the sample. For example, a first primer sequence corresponding to the nucleotide sequence set forth at SEQ ID NO:1 from position 1201-1220 could be used as a forward primer in a thermal amplification reaction with a second primer sequence corresponding to the reverse complement of the nucleotide sequence as set forth at SEQ ID NO:1 from position 1581-1600. Such primers when used together in a thermal amplification reaction with a biological sample containing SEQ ID NO:1 would result in the synthesis of an amplicon corresponding to SEQ ID NO:1 from nucleotide position 1201 through 1600, i.e., a 400 nucleotide amplicon, which would contain the 20 nucleotide segment from nucleotide position 1401-1420 as set forth in SEQ ID NO:1, and would therefore be diagnostic for the presence of the Cry1A.105 coding sequence in such sample.

A kit for detecting the presence of a Cry1A.105 or detecting the presence of a nucleotide sequence encoding a Cry1A.105 in a sample is provided. The kit is provided along with all reagents and control samples necessary for carrying out a method for detecting the intended agent, as well as instructions for use.

The following examples describe preferred embodiments of the invention. Other embodiments within the scope of the claims will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

Example 1

This example illustrates synthetic nucleotide sequences encoding an insecticidal Cry1A.105 protein.

A nucleotide sequence as set forth at SEQ ID NO:1 encoding a Cry1A.105 insecticidal protein was constructed for use in dicotyledonous plants. The amino acid sequence translation is set forth at SEQ ID NO:2. The toxin encoding segment consists of nucleotides from about position 1 through about position 1830, more or less.

A nucleotide sequence as set forth at SEQ ID NO:3 encoding a Cry1A.105 amino acid sequence was constructed for expression in monocotyledonous plants. The amino acid sequence translation is set forth at SEQ ID NO:4. The toxin encoding segment consists of nucleotide from about position 1 through about position 1830, more or less.

The nucleotide sequences as set forth at SEQ ID NO:1 and SEQ ID NO:3 are substantial equivalents of each other. SEQ ID NO:1 and SEQ ID NO:3 exhibit an overall identity of about 94.3%. The two coding sequences are identical from about nucleotide position 1330 through the nucleotide position 3534. The toxin encoding portion of each sequence consists of from about nucleotide position 1 through nucleotide position 1830, and these segments exhibit about 88.9% identity to each other. The substantial differences between the two sequences lie within from about nucleotide position 1 through about nucleotide position 1329, or about the first two thirds of the segment encoding the toxin portion of the Cry1A.105 protein. The two sequences exhibit about 84.7% identity throughout this segment.

An *E. coli* strain (TOP10, Invitrogen, Inc.) transformed with a plasmid designated as pMON70522 containing a beta-lactamase selectable marker and a sequence as set forth at SEQ ID NO:3 encoding a Cry1A.105 was deposited on Aug. 31, 2005, with the Agriculture Research Culture Collection (NRRL) International Depository Authority at 1815 North University Street, in Peoria, Ill. 61604 U.S.A., according to the Budapest Treaty on the International Recognition of the Deposit of Microorganisms for the Purpose of Patent Procedures and was designated as NRRL B-30873.

Example 2

This example illustrates transgenic cotton plants expressing a Cry1A.105 protein.

Delta and Pineland DP50 cotton seeds were surface sterilized and germinated overnight. Meristem explants were isolated and the primary leaves were removed by micro dissection. Dissected explants were placed in a targeting medium such that the meristems were oriented perpendicular to the direction of the particle delivery. The transformation vector, pMON47740, comprises an expression cassette having a nucleotide sequence set forth in SEQ ID NO:9. A KpnI fragment containing a GUS marker gene under the control of an e35S promoter and a chloroplast targeted Cry1A.105 coding sequence under the control of an eFMV promoter was excised from this plasmid and isolated by HPLC and used for gun transformation of the cotton meristem explants. Purified DNA containing both the Cry1A.105 expression cassette and the GUS marker was precipitated onto microscopic gold beads and coated in a thin layer onto a Mylar sheet. The DNA was accelerated into the meristem tissue by electric discharge particle delivery under a partial vacuum. Following bombardment, explants were de-targeted onto hormone-free media without a selective agent. Leaf tissues from regenerated plantlets were sampled and assayed for expression of the GUS marker. Transgenic plants exhibiting a high level of GUS expression were sent to the greenhouse for further screens. These plants were again tested for expression of GUS and negative portions of the plants were pruned off. This cycle of sampling and pruning of GUS-negative tissues was repeated until all sectors of from each plant were positive for the GUS marker. The plants were then maintained under standard greenhouse conditions until seed harvest.

Tissues obtained from F1 GUS positive transgenic cotton plants were tested in bioassays for insecticidal activity against cotton bollworm (CBW) and fall armyworm (FAW). Previously generated isogenic cotton plants expressing insecticidal levels of Cry1Ac or a combination of Cry1Ac and Cry2Ab were used as positive controls and a non-transgenic isoline was used as the negative control.

CBW square assays were used as one means for determining insecticidal activity of the transgenic cotton plants. (Adamczyk et al., (2001) J. Econ. Entomol. 94:284-290; Kranthi et al (2005) Current Science 89:291-298). Squares of leaf tissue (match head size or larger) were collected and placed individually in assay wells. Each square was infested with a single third-instar CBW larva. The number of surviving insects was recorded five days after infestation.

CBW boll assays were also used to determine the insecticidal activity of boll tissue collected from the transgenic plants. 8 hard green bolls (post bloom) from each event were collected and placed in individual cups and infested with third instar CBW larvae. The number of surviving insects was recorded five days after infestation.

Leaf assays were conducted to determine the insecticidal activity of transgenic leaf tissue against FAW. New leaves were taken from terminals of cotton plants. 2 leaf punches, each about ¾" in diameter, were collected and placed in each of 16 individual assay wells. Each well was infested with a single second or third instar FAW larva. The number of surviving insects was recorded five days after infestation.

Bioassay results are shown in Table 1. The results show that transgenic cotton events expressing Cry1A.105 exhibited greater insecticidal activity than transgenic events expressing either Cry1Ac or a combination of Cry1Ac and Cry2Ab against both FAW and CBW.

TABLE 1

Bioassay results of FAW and CBW using the transgenic cotton plant tissue.

| Plant | FAW (% survival) (leaf tissue) | CBW (% survival) (Square tissue) | CBW (% survival) (Boll tissue) |
|---|---|---|---|
| Cry1Ac/Cry2Ab | 74.5 | 32.0 | 35.8 |
| Cry1Ac | 92.7 | 35.5 | 35.8 |
| Isoline | 99.6 | 96.8 | 54 |
| 17238 | 10.9 | 9.4 | 25 |
| 17567 | 0 | 12.5 | 12.5 |
| 17774 | 1.6 | 1.2 | 0 |
| 17875 | 3.1 | 4.2 | 0 |
| 18026 | 1.6 | 18.8 | 12.5 |
| 18122 | 7.8 | 22.9 | 0 |

Tobacco budworm and corn earworms were also tested in similar bioassays. In each case, the Cry1A.105 plants exhibited insecticidal activity against these pests as well.

Example 3

This example illustrates transgenic corn plants expressing a Cry1A.105 protein.

Transgenic corn plants were regenerated from cells transformed with the vector pMON40232. pMON40232 contains an expression cassette having a nucleotide sequence as set forth in SEQ ID NO:7 that contains, in operable linkage, an enhanced CAMV 35S promoter, a wheat CAB leader sequence, a rice actin 1 intron, a Cry1A.105 coding sequence and a wheat hsp17 gene 3' transcription termination and polyadenylation sequence. A nucleotide sequence encoding an *Arabidopsis thaliana* EPSPS chloroplast targeting sequence (At.EPSES-CTP2) is positioned upstream of and in frame with the Cry1A.105 coding sequence. pMON40232 contains a recombinant gene encoding an EPSPS that is insensitive to the herbicide glyphosate, for use in selection of transgenic events. Transgenic events arising from tissue transformed with pMON40232 were designated as LAJ 105. Transgenic events were screened for the absence of any vector backbone, for the presence of a single simple inserted sequence, and for the intactness of the expression cassette containing the nucleotide sequence encoding the Cry1A.105 protein.

Bioassays were conducted with events that met the limitations of the event screen. LAJ105 transgenic corn plants were compared in the bioassay to an isogenic LH198 negative control and a positive control MON810 variety expressing the insecticidal portion of a Cry1Ab protein. Five leaf disks, each about one centimeter in diameter, were obtained from each of 10 individual Cry1A.105 transgenic events and from the controls. Leaf disks were placed on agar filled wells to keep the plant material turgid. Discs were then subjected to feeding by FAW, black cutworm (BCW), European corn borer (ECB), corn earworm (CEW), and Southwestern corn borer (SWCB) neonate larvae. A single neonate FAW larvae, a single CEW larvae, two neonate BCW, two neonate SWCB larvae, or four neonate ECB larvae were applied to each well. Feeding damage was evaluated after four days, using a leaf damage rating (LDR) scale from 0-11, 0 indicating no visible feeding damage, 11 indicating at least 50% of the disc was eaten, and each point on the scale between 0 and 11 indicating a 5% increase in observed feeding damage to the leaf disc under observation.

Bioassay results indicated that events expressing Cry1A.105 protein exhibited greater insecticidal activity toward FAW, ECB and CEW than the LDR's exhibited by the Cry1Ab control against the same pest larvae. LDR's for these three pests on the Cry1A.105 events was less than 1 while the Cry1Ab control exhibited LDR's ranging from about 8 to about 10. The LDR was consistently between 1 and 2 both for the Cry1A.105 events and for the Cry1Ab control when tested for activity against SWCB, indicating that the Cry1A.105 protein was no more toxic to SWCB than was Cry1Ab. The results of this bioassay supported previous results that indicated that Cry1Ab is ineffective in controlling BCW. The Cry1A.105 events were no more effective against BCW than was the Cry1Ab control. Thus, at the levels of expression of the Cry1A.105 protein in planta, these plants would be effective in controlling other lepidopteran genus plant pests including but not limited to those in the genus *Anticarsia, Pseudoplusia, Rachiplusia, Heliothis, Helicoverpa, Spodoptera, Epinotia,* and *Armigera*.

What is claimed is:

1. A synthetic polynucleotide encoding an insecticidal protein comprising the amino acid sequence as set forth in SEQ ID NO:2 from amino acid position 10 through amino acid position 600.

2. The synthetic polynucleotide of claim 1 selected from the group consisting of SEQ ID NO:1 and SEQ ID NO:3.

3. The synthetic polynucleotide of claim 2, wherein said polynucleotide is SEQ ID NO:3 for use in expressing said insecticidal protein in a monocotyledonous crop plant.

4. The synthetic polynucleotide of claim 2, wherein said polynucleotide is SEQ ID NO:1 for use in expressing said insecticidal protein in a dicotyledonous crop plant.

5. A synthetic insecticidal protein comprising the amino acid sequence as set forth in SEQ ID NO: 2 from amino acid position 10 through amino acid position 600.

6. A composition comprising an insecticidally effective amount of the synthetic insecticidal protein of claim 5.

7. An expression cassette for use in expressing an insecticidal protein having the amino acid sequence as set forth in SEQ ID NO:2 in a host cell, wherein said expression cassette comprises in operable linkage a promoter sequence functional in said host cell and a polynucleotide encoding said protein.

8. The expression cassette of claim 7, wherein said host cell is selected from the group consisting of a bacterial cell, a fungal cell, a mammalian cell, and a plant cell.

9. The expression cassette of claim 8, wherein (a) said bacterial cell is selected from the group consisting of a *Bacillus* species cell, a Enterobacteriacae species cell, a *Pseudomonas* species cell, a *Clostridium* species cell, and a *Rhizobium* species cell, and a *Agrobacterium* species cell; and (b) said plant cell is selected from the group of plants consisting of a dicotyledonous plant and a monocotyledonous plant, said dicotyledonous plant being further selected from the group consisting of alfalfa, apple, apricot, asparagus, bean, berry, blackberry, blueberry, canola, carrot, cauliflower, celery, cherry, chickpea, citrus tree, cotton, cowpea, cranberry, cucumber, cucurbit, egg plant, fruit tree, grape, lemon, lettuce, linseed, melon, mustard, nut bearing tree, okra, orange, pea, peach, peanut, pear, plum, potato, soybeans, squash, strawberry, sugar beet, sunflower, sweet potato, tobacco, tomato, turnip, and vegetable, and said monocotyledonous plant being further selected from the group consisting of corn, wheat, oat, rice, sorghum, milo, buckwheat, rye, fescue, timothy, brome, orchard, St. Augustine, Bermuda, bentgrass, and barley.

10. The expression cassette of claim 7, wherein said host cell is a plant cell and said expression cassette further comprises in operable linkage a polynucleotide selected from the group consisting of an expression enhancer sequence, an untranslated leader sequence, an intron sequence, a chloroplast targeting peptide encoding sequence, and a transcription termination and polyadenylation sequence.

11. A vector comprising the expression cassette of claim 7.

12. A transgenic plant or plant cell resistant to lepidopteran insect infestation comprising a polynucleotide encoding a protein exhibiting the amino acid sequence as set forth in SEQ ID NO:2 from amino acid position 10 through amino acid position 600, wherein said protein exhibits insecticidal activity when expressed in said plant or plant cell.

13. The transgenic plant or plant cell of claim 12, wherein said transgenic plant is selected from the group consisting of a dicotyledonous plant and a monocotyledonous plant, said dicotyledonous plant being further selected from the group consisting of alfalfa, apple, apricot, asparagus, bean, berry, blackberry, blueberry, canola, carrot, cauliflower, celery, cherry, chickpea, citrus tree, cotton, cowpea, cranberry, cucumber, cucurbit, egg plant, fruit tree, grape, lemon, lettuce, linseed, melon, mustard, nut bearing tree, okra, orange, pea, peach, peanut, pear, plum, potato, soybeans, squash, strawberry, sugar beet, sunflower, sweet potato, tobacco, tomato, turnip, and vegetable, and said monocotyledonous plant being further selected from the group consisting of corn, wheat, oat, rice, sorghum, milo, buckwheat, rye, fescue, timothy, brome, orchard, St. Augustine, Bermuda, bentgrass, and barley.

14. The transgenic plant or plant cell of claim 13 resistant to lepidopteran insect infestation, wherein said lepidopteran insect is selected from the group consisting of a leaf roller, a cutworm, an armyworm, a borer, a bagworm, and a forage feeder.

15. The transgenic plant or plant cell of claim 14, wherein said lepidopteran insect is further selected from the group consisting of a fall armyworm, a European corn borer, a corn earworm, cotton bollworm, and a southwestern corn borer.

16. A progeny or seed of the transgenic plant or plant cell of claim 13, wherein said progeny or seed comprise said polynucleotide.

17. A method for controlling lepidopteran insect infestation of a plant, said method comprising providing in the diet of the insect one or more plant cells transformed with a nucleic acid comprising in operable linkage a plant functional promoter and a polynucleotide encoding a protein that exhibits the amino acid sequence as set forth in SEQ ID NO:2 from amino acid position 10 through amino acid position 600 exhibiting lepidopteran insecticidal activity.

18. The expression cassette of claim 10 comprising a polynucleotide selected from the group consisting of SEQ ID NO:5 and SEQ ID NO:7.

19. A synthetic polynucleotide encoding an insecticidal protein exhibiting the amino acid sequence as set forth at SEQ ID NO:2 from about amino acid 1 through about amino acid 612.

20. A synthetic polynucleotide encoding the insecticidal protein as set forth at SEQ ID NO:2 from about amino acid 1 through about amino acid 610.

21. The synthetic polynucleotide of claim 19 exhibiting at least about 90% identity to the nucleotide sequence as set forth at SEQ ID NO:1.

22. The synthetic polynucleotide of claim 19 exhibiting at least about 90% identity to the nucleotide sequence as set forth at SEQ ID NO:3.

23. A hybrid insecticidal protein comprising an amino acid segment comprising from about 500 to about 600 contiguous amino acids selected from the amino acid segment as set forth at SEQ ID NO:2 from about amino acid position 10 through about amino acid position 600.

24. A composition comprising an insecticidally effective amount of a Cry1A.105 protein exhibiting the amino acid sequence as set forth in SEQ ID NO:2 from about amino acid position 10 through about amino acid position 600, wherein said composition is selected from the group consisting of a plant cell, a bacterial cell, a fungal cell, a colloid, an emulsion, a seed coating, a bait, and a powder.

25. The composition of claim 24, wherein said Cry1A.105 protein is present in an amount from about 0.5 to about 200 parts per million (PPM).

26. The composition of claim 25, wherein said Cry1A.105 protein is present in an amount from about 0.5 to about 20 PPM.

27. The composition of claim 25, wherein said composition is a plant cell or a group of plant cells.

28. The composition of claim 27, wherein the insecticidally effective amount of said Cry1A.105 protein is encoded by a polynucleotide which is present in an amount detectable using a probe that is or is complementary to a sequence selected from the group consisting of SEQ ID NO:1 from nucleotide position 1401-1420 and SEQ ID NO:1 from nucleotide position 1821-1840.

29. The composition of claim 27, wherein said insecticidally effective amount of said protein is sufficient to control a lepidopteran genus plant pest when provided in the diet of said pest, said pest being selected from the group consisting of *Anticarsia*, *Pseudoplusia*, *Rachiplusia*, *Heliothis*, *Helicoverpa*, *Spodoptera*, *Epinotia*, and *Armigera*.

30. A method for protecting a crop in a field from lepidopteran insect infestation, said method comprising providing a transgenic crop plant comprising an insecticidally effective amount of a Cry1A.105 protein insecticidal agent in the diet of the lepidopteran insect to inhibit the insect from surviving on said transgenic crop plant, wherein said insecticidal agent comprises the amino acid sequence from about amino acid position 10 through about amino acid position 600 as set forth in SEQ ID NO:2.

31. The method of claim 30, wherein said transgenic crop plant further comprises an additional insecticidal agent toxic to the same insect species as the Cry1A.105 and is selected from the group consisting of a *Bacillus* toxin, a *Xenorhabdus* toxin, a *Photorhabdus* toxin, and a dsRNA specific for suppression of one or more essential genes in said insect species.

32. The method of claim 30 or 31, wherein the yield of said crop is improved compared to the yield of an isogenic crop lacking said insecticidal agent or agents.

33. The method of claim 31, wherein said additional insecticidal agent is a *Bacillus* toxin selected from the group of proteins consisting of a Cry1, a Cry2, a Cry5, a Cry9 toxin, and a VIP protein.

34. A method for delaying the onset of resistance to a lepidopteran species, said method comprising providing a Cry1A.105 first insecticidal protein with at least a second insecticidal protein different from the first, wherein said second insecticidal protein is selected from the group of proteins consisting of a Cry1, a Cry2, a Cry5, a Cry9 toxin, and a VIP protein.

* * * * *